United States Patent
Kauvar et al.

(10) Patent No.: US 9,321,830 B2
(45) Date of Patent: *Apr. 26, 2016

(54) ANTI-RSV G PROTEIN ANTIBODIES

(71) Applicant: TRELLIS RSV HOLDINGS, INC., South San Francisco, CA (US)

(72) Inventors: Lawrence M. Kauvar, San Francisco, CA (US); Ellen J. Collarini, Oakland, CA (US); Bruce Keyt, Hillsborough, CA (US); Orit Foord, Foster City, CA (US)

(73) Assignee: Trellis RSV Holdings, Inc., South San Francisco, CA (US)

( * ) Notice: Subject to any disclaimer, the term of this patent is extended or adjusted under 35 U.S.C. 154(b) by 318 days.

This patent is subject to a terminal disclaimer.

(21) Appl. No.: 13/626,852

(22) Filed: Sep. 25, 2012

(65) Prior Publication Data

US 2013/0034564 A1 Feb. 7, 2013

Related U.S. Application Data

(63) Continuation of application No. 12/778,933, filed on May 12, 2010, now Pat. No. 8,273,354, which is a continuation of application No. 12/258,260, filed on Oct. 24, 2008, now Pat. No. 7,736,648.

(60) Provisional application No. 61/089,401, filed on Aug. 15, 2008, provisional application No. 61/000,469, filed on Oct. 25, 2007.

(51) Int. Cl.
*A61K 39/42* (2006.01)
*C07K 16/10* (2006.01)
*A61K 39/00* (2006.01)

(52) U.S. Cl.
CPC ....... *C07K 16/1027* (2013.01); *A61K 2039/505* (2013.01); *C07K 2317/21* (2013.01); *C07K 2317/24* (2013.01); *C07K 2317/34* (2013.01); *C07K 2317/54* (2013.01); *C07K 2317/76* (2013.01); *C07K 2317/92* (2013.01); *C12N 2740/11011* (2013.01)

(58) Field of Classification Search
CPC ................. A61K 2039/505; C07K 16/1027; C07K 2317/21; C07K 2317/24
See application file for complete search history.

(56) References Cited

U.S. PATENT DOCUMENTS 7,736,648 B2 * 6/2010 Kauvar et al. ............... 424/147.1
8,273,354 B2 * 9/2012 Kauvar et al. ............... 424/139.1
2006/0018925 A1 1/2006 Tripp et al.
2009/0004198 A1 1/2009 Nakajima et al.

FOREIGN PATENT DOCUMENTS

| FR | 2 766 192 | 1/1999 |
| WO | WO-00/43040 | 7/2000 |
| WO | WO-02/32942 | 4/2002 |
| WO | WO-2007/094423 | 8/2007 |
| WO | WO-2007/101441 | 9/2007 |

OTHER PUBLICATIONS

Anderson et al., Journal of Clinical Microbiology (1986) 23(3):475-480.
Anderson et al., J. Virol. (1988) 62:4232-4238.
Corbeil et al., Vaccine (1996) 14:521-525.
Garcia et al., J. Virol. (1994) 68(9):5448-5459.
Genbank accession No. ABZ81097.1 (Jul. 1, 2008).
Genbank accession No. ABZ81098.1 (Jul. 1, 2008).
Harcourt et al., J.I.D. (2004) 190:1936-1940.
Harcourt et al., J. Immunol. (2006) 176:1600-1608.
Harris, Biochemical Society Transactions (1995) 23:1035-1038.
Haynes et al., J. Virol. (2003) 77:9831-9844.
Houdebine, Current Opinions in Biotechnology (2002) 13:625-629.
Hurle et al., Current Opinion in Biotechnology (1994) 5:428-433.
International Search Report and Written Opinion for PCT/US08/81175, mailed Jun. 30, 2009, 7 pages.
Johnson et al., PNAS USA (1987) 84(16):5625-5629.
Mekseepralard et al., J. Gen. Virol. (2006) 87:1267-1273.
Plotnicky-Gilquin et al., J. Virol. (1999) 73(7):5637-5645.
Polack et al., PNAS USA (2005) 102:8996-9001.
Power et al., Vaccine (2001) 19:2345-2351.
Routledge et al., J. Gen. Virol. (1988) 69:293-303.
Shingai et al., Int'l Immunology (2008) epub Jul. 8.
Sidwell et al., Antiviral Research (2006) 71:379-390.
Stott et al., J. Virol. (1986) 60:607-613.
Sullender, Virol. (1995) 209:70-79.
Taylor et al., Immunol. (1994) 52:137-142.
Tripp et al., Nature Immunology (2001) 2:732-738.
Walsh et al., Infect. Immun. (1984) 43:756-758.
Walsh et al., J. Gen. Virol. (1989) 70:2953-2961.
Walsh et al., J. Gen. Virol. (1998) 79(3):479-497.
Whitehead et al., Vaccine Candidates J. Virol. (1999) 73(12):9773-9780.
Winter et al., Immunology Today (1993) 14:243-246.
Yu et al., J. Virol. (2008) 82:2350-2357.
Carter et al., "Humanization of an anti-p185$^{HER2}$ antibody for human cancer therapy," PNAS USA (1992) 89:4285-4289.
Decision of Rejection (translation) for JP 2010-531283, mailed Sep. 16, 2014, 4 pages.
Foote et al., "Antibody Framework Residues Affecting the Conformation of the Hypervariable Loops," J. Mol. Biol. (1992) 224:487-499.

* cited by examiner

*Primary Examiner* — Jeffrey Parkin
(74) *Attorney, Agent, or Firm* — Morrison & Foerster LLP

(57) ABSTRACT

Individual monoclonal antibodies and fragments that bind a conserved epitope of the G protein of RSV and which are minimally immunogenic when administered to a human subject, are useful in treating RSV infections.

16 Claims, 21 Drawing Sheets

*Representative Probe of Peptide Array Underlying the Epitope Definition.*

*Epitope Recognized by Murine 131-2G = Residues 163-168 of RSV-A2 Strain*

```
 97    SKPNNDF HFEVF
 98    KPNNDF HFEVF N
 99    PNNDF HFEVF NF
100    NNDF HFEVF NFV
101    NDF HFEVF NFVP
102    DF HFEVF NFVPS
103    F HFEVF NFVPSS
104    HFEVF NFVPSSI
```

*Alignment of the 131-2G Epitope within the G Protein Sequence*

```
                 151           1312G           CX3C              200
RSV-G S2  (151)  RQNKPPNKPNNDF HFEVF NFVPCSICSNNPT CWAIC KRIPNKKPGKKTT
RSVA 1734 (151)  RQNKPPSKPNNDF HFEVF NFVPCSICSNNPT CWAIC KRIPNKKPGKRTT
   RSVA2  (151)  RQNKPPSKPNNDF HFEVF NFVPCSICSNNPT CWAIC KRIPNKKPGKKTT
    RSVB  ( 91)  RSKNPPKKPKDDY HFEVF NFVPCSICGNNQL CKSIC KTIPSNKPKKKPTI
```

*FIG. 3*

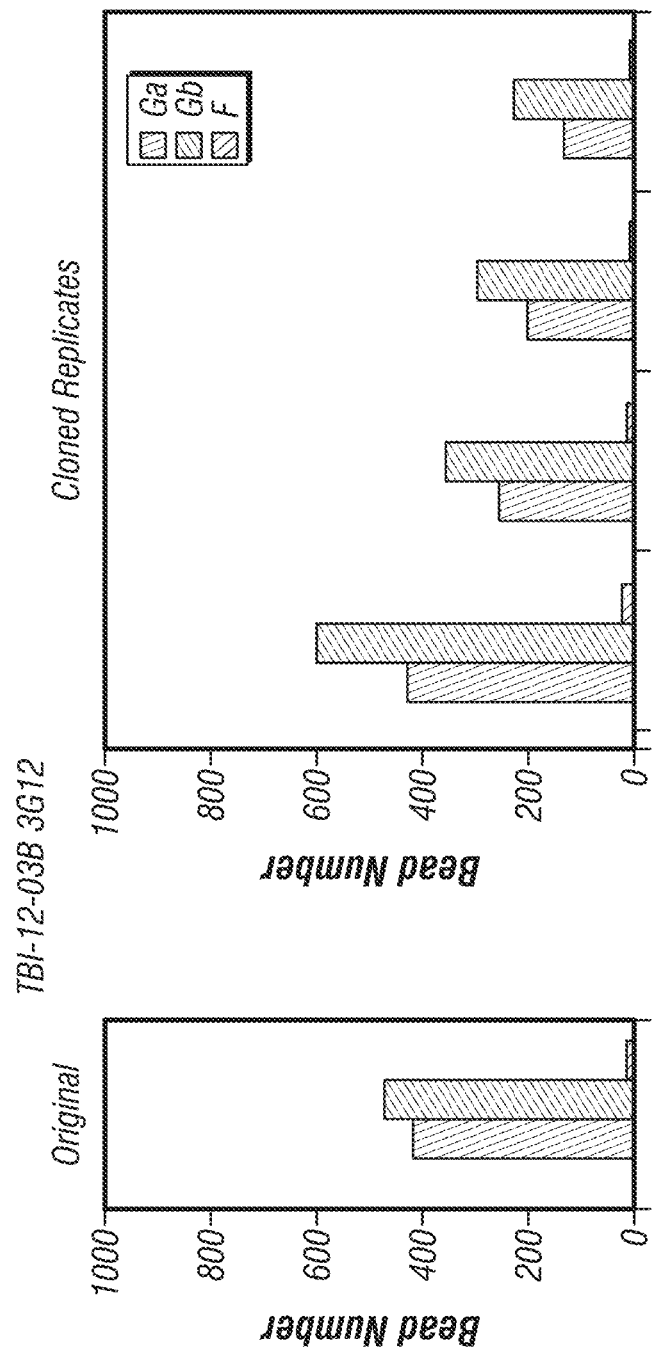

| Bin | VH | J | JH | FR1 | CDR1 | FR2 | CDR2 |
|---|---|---|---|---|---|---|---|
| 1F12 | VH1-46 | D3-10 | JH4 | QVQLVQSESEVKKPGASVTVSCKPSGYTFN | T--YYIH | WVRQAPGQGLEWMG | VINP---SGGSTYYTQRFQD |
| 3G12 | VH4-39 | D3-10 | JH5 | QLQLQESGPGLVKPSETLSLTCTVSGGSIS | SSNYYWG | WIRQPPGKGLEWIA | SIH----DSGSIYYNPSLRS |
| 1A5 | VH4-39 | D6-13 | JH5 | QLQLQESGPGLVKPSETLSLTCTVSGDSIT | SGQYYWA | WIRQAPGKGLEWIG | SIH----YSGSTYQNPSLKS |
| 3D3 | VH3-9 | D5-12 | JH6 | EEQLVESGGGIVQPGRSLRLSCVGSGLRFE | E--HAMH | WVRQAPGKGLEWVS | GISW---NSGSVGYADSVKG |
| 1G1 | VH1-18 | D3-3 | JH4 | QVHLVQSGGGVEVKKPGASVRVSCKASGYTFA | T--YGIT | WVRQAPGRGLEWVG | WITP---YNDRTSYAQIFHG |
| 2B11 | VH1-69 | D2-21 | JH6 | QVQLVQSGAEVKKPGSSVKPCKASGGTFS | T--YPIS | WVRQAPGQGLEWMG | RIIP---DPPMANIAQKFQG |
| 5D8 | VH3-30 | D4-23 | JH6 | QAQLVESGGGVVQPGRSLRLSCAASGFTFS | V--SMGH | WVRQAPGRGLEWLA | VISY---DGNKMYYADSVKG |
| 2D10 | VH1-18 | D6-19 | JH4 | QVQLVQSGAEVKKPGASVKVSCKASGYVFT | N--YGVS | WVRQAPGQGLEWMG | WSSP---YNGNFYYAQKLKA |
| 3F9 | VH1-18 | D6-25 | JH6 | QVQLVQSGAELKKPGASVKVSCKASGYTFI | N--YAIS | WVRQAPGQGLEWMG | WISA---YNGNTHYAQKVQD |
| 1D4 | VH1-46 | D6-19 | JH2 | QLQLQESGPGLVKPSETLSLTCTVSGDSIT | T--YYIH | WIRQAPGKGLEWIG | VINP---SGGSTYYAQKFQD |
| 1G8 | VH4-39 | D6-13 | JH5 | QLQLQESGGGIVQPGGSLRLSCVASGFTFS | SGQYYWA | WIRQPPGKGLEWIG | SIH----YSGSTYQNPSLKS |
| 6A12 | VH3-74 | D2-15 | JH3 | EVQVVESGGGLVQPGRSLRLSCEAASGFTFS | S--YWMH | WVRQAPAKGLEWVA | RIYS---DGSSTYADSVKG |
| 10C6 | VH3-30.5 | D6-19 | JH3 | QVQLVQSGAEVKKPGASVKVSCKASGYSFT | G--YAMH | WVRQATGQGLEWMG | VISF---DGSNNYYADSVKG |
| Hu 131-2G | VH1-8 | | | | G--FTMN | WVRQATGQGLEWMG | LINP---FNGNTGYNQKFKG |

| Bin | FR3 | CDR3 | J |
|---|---|---|---|
| 1F12 | RVTMFTDTSTNTIYMDLTSLRSDDTAMYYCVR | GSNLLPHLWEWKPSHFDS | WGQGTLVTVSS |
| 3G12 | RLTTSVDTSKNQFSLKLSSVTAADTAVYYCAR | HLVWFGELRNNWFDP | WGQGTLVTVSS |
| 1A5 | RFTTSVDTSRDQISMKLSSVTVAESAVYYCAR | QQLSLSPVENWFDP | WGKGTTVTVSS |
| 3D3 | RVTMFTDTSTNTAYMELRSEDTALYFCAI | MVATTKNDFHYYKDV | WGQGTLVSVSS |
| 1G1 | RVTMFTDTSTNTAYMELRSLSEDTAVYYCAR | NHCNFYHDFWSGLDY | WGQGTMVAVSS |
| 2B11 | RVSFSADKSTTIVYMELSSLRSEDTAVFCAR | EIILQSPPFAVDV | WGQGTMVTVSS |
| 5D8 | RFTTSRDNSKMTLYLQMNSLRRREDTAVYFCAR | DGLDYGGDLVYGNMDV | WGNGTTVTVSSAS |
| 2D10 | RFTTSRDNSKNTLYLQMNSLRAEDTAVYYCAR | DMLGVVQAVAGPFDS | WGQGTTVTVSSAS |
| 3F9 | RVTLTDTSTRTVYMDLSLRSEDTAVYYCAR | IPLLGYSSGWYAFDM | WRQGTMPVSSAS |
| 1D4 | RITLTDTSTRTVYMDLSLRSEDTAVYYCAR | VHKGRAEQWQLLHGHFDL | WGRGSLVTVSS |
| 1G8 | RFTTSVDTSRDQISMKLSSVTVAESAVYYCAR | QQLSLSPVENWFDP | WGQGTLVTVSSAS |
| 6A12 | RFTTSRDNAKNTLYLQMNLFLQMNSLRAEDTAVYYCVR | VLGAAMFDI | WGQGTMVTVSSAS |
| 10C6 | RFTTSRDNSKNMLFLQMNSLRAEDTAVYYCAR | PDVIAVAGTALSNPFDL | WGLGTMVTVSSAS |
| Hu 131-2G | RVTMFRNTSISTAYMELSSLRSEDTAVYYCAR | SGKSYDYEAWFTY | WGQGTLVTVSA |

| Bin | V | J | FR1 | CDR1 | FR2 | CDR2 |
|---|---|---|---|---|---|---|
| 1F12 | VK A27 | JK3 | EIVLTQSPGTLSLSPGERATLSC | RASQSTTNN----YLA | WYQQKPGQAPRLLIY | DSFSRAT |
| 3G12 | VKL2 | JK3 | EIVMTQSPATLSVSPGERATLSC | RASQSVNS-----NLA | WYQHKPGQAPRLLIY | GASTRAT |
| 1A5 | VKL2 | JK3 | EIVVTQSPVTLSVSPGESATLSC | RSARSVGS-----RLA | WYQQKPGQPPRLLIF | AASTRAT |
| 3D3 | VK L6 | JK2 | QIVLTQSPATLSLSPGERATLSC | RASQSVSN-----HLA | WYQQKPGQAPRLLIY | ESTNRAT |
| 1G1 | VL3-25 | JL1 | SFELTQPPSVSVSPGQTARITC | SG-DA-LPKQ-YVY | WYQQKPGAPVLVIY | KTTERPS |
| 2B11 | VL1-4 | JL1 | QSALTQPASVSGSPGQSITISC | TGSSSDVGGYSHVS | WYQQHPGKVPKLIIS | EVSNRPS |
| 5D8 | VL3-25 | JL1 | SYELTQPPSVSVSPGQTGRITC | TGSEASGDALASRYAY | WYQHKSGQAPVVLIY | KDTERPS |
| 2D10 | VKL5 | JK3 | DTPMTQSPSSSVSASVGDRVTISC | RASQGISN-----SLA | WYQQLGKAPQLLIY | AASSLQS |
| 3F9 | VL1-2 | JL3 | QSALTQPPSASGSPGQSVTISC | TGTSSDVGGYNYVS | WYQQHPGKAPKLMIY | EVNKRPS |
| 1D4 | VK B3 | JK2 | DIVMTQSPDSLAVSLGERATINC | KSSQSVLYSSNNKTYLA | WYQKPGQPPELLIY | WASTRES |
| 1G8 | VKL2 | JK3 | EIVVTQSPVTLSVSPGESAALSC | RASRSVGS-----RLA | WYQQKPGQPPRLLIF | AASTRES |
| 6A12 | VKL6 | JK3 | EIVLTQSPATLSLSPGERATLSC | RASQSVSS-----YLA | WYQQKPGQAPRLLIS | DASNRAT |
| 10C6 | VKL2 | JK5 | EIVLTQSPATLSLSPGERALSC | RASQSVRS-----NLV | WYQQKPGQAPLLIY | GASTRAT |
| Hu 131-2G | VK | | DIVMTQTPLSLSVTPGQPASISC | RSSQTIVHTNGNTYLE | WYLQKPGQSPQLLIY | KVSNRFS |

| Bin | FR3 | CDR3 | J |
|---|---|---|---|
| 1F12 | GIPERFSGSGSGTDFTLTISRLEPEDFAVYYC | QHYVRSPLT | FGPGTKVEIKR |
| 3G12 | GIPARFSGSGSGTDFTLTISSLQSEDFAVYYC | QQYNNWPL | FGPGTKVDLKR |
| 1A5 | GIPARFSGSGSGTDFTLIISGLQSEDYAVYYC | QQYKEWPL | FTFGPGTTVDSKR |
| 3D3 | GIPPRFSGSGSGTDFTLTISSLEPEDFAVYYC | QQRNNWYT | FGQGTKLEIK |
| 1G1 | GIPERFSDSSSGSGTTVLTISAAQAEDEADYYC | QSVDSSGTY | VFGIGTKVTVLS |
| 2B11 | GTSNRFSGSKSANTASLTISGLQPEDEADYYC | GSYASTNLH | YVFGTGTKVTVLS |
| 5D8 | GISERFSGSSGTTVLTIISGVLAEDEADYYC | KTSVRNGTSW | VFGTGTMLFVLR |
| 2D10 | GVPSRFSGSGSGTDFTLTISSLQPEDEATYYC | QQTNTFP | FTFGPGTKVEVRR |
| 3F9 | GVPDRFSGSGSGNTASLTVSGLQAEDEAEYYC | SSYAGSMNW | VFGGTKLTVLG |
| 1D4 | GVPDRFSGSGSGTNFTLTISSLQSEDYAVYYC | QQYYTTP | YTFGQGTKLEIKR |
| 1G8 | GIPARFSGSGSGTDFTLIISGLQSEDFAVYYC | QQYKEWPL | FTFGPGTTVDSKR |
| 6A12 | GIPDRFSGSGSGTDFTLTISSLEPEDFAVYYC | QQRSNWPP | RFTFGPGTIVDIRR |
| 10C6 | GIPARFSGSGSGTDFTLTISSLQSEDFALYFC | QQNNWPP | TFGQGTRLEIKR |
| Hu 131-2G | GVPDRFSGSGSGTDFTLKISRVEAEDVGVYYC | FQGSHVPFT | FGSGTKLEIKR |

HuMab Binds RSV, Doesn't Come Off

SEQUENCE LISTING

```
<160> NUMBER OF SEQ ID NOS: 56

<210> SEQ ID NO 1
<211> LENGTH: 13
<212> TYPE: PRT
<213> ORGANISM: Artificial Sequence
<220> FEATURE:
<223> OTHER INFORMATION: respiratory syncytial virus A2 strain

<400> SEQUENCE: 1

His Phe Glu Val Phe Asn Phe Val Pro Cys Ser Ile Cys
 1               5                  10

<210> SEQ ID NO 2
<211> LENGTH: 6
<212> TYPE: PRT
<213> ORGANISM: Artificial Sequence
<220> FEATURE:
<223> OTHER INFORMATION: respiratory syncytial virus A2 strain

<400> SEQUENCE: 2
```

Phe Glu Val Phe Asn Phe
1               5

<210> SEQ ID NO 3
<211> LENGTH: 10
<212> TYPE: PRT
<213> ORGANISM: Artificial Sequence
<220> FEATURE:
<223> OTHER INFORMATION: respiratory syncytial virus A2 strain

<400> SEQUENCE: 3

Val Phe Asn Phe Val Pro Cys Ser Ile Cys
1               5                   10

<210> SEQ ID NO 4
<211> LENGTH: 423
<212> TYPE: DNA
<213> ORGANISM: Mus musculus
<220> FEATURE:
<221> NAME/KEY: misc_feature
<222> LOCATION: (1)...(423)
<223> OTHER INFORMATION: heavy chain V segment of IgH-VJ558 family
<220> FEATURE:
<221> NAME/KEY: CDS
<222> LOCATION: (1)...(423)

<400> SEQUENCE: 4 atg gga tgg agc tgg atc ttt ctc ttc ctc ctg tca gga act gca ggt     48
Met Gly Trp Ser Trp Ile Phe Leu Phe Leu Leu Ser Gly Thr Ala Gly
1               5                   10                  15 gtc cac tct gag gtc cag ctg caa cag tct gga cct gaa ctg gtg aag     96
Val His Ser Glu Val Gln Leu Gln Gln Ser Gly Pro Glu Leu Val Lys
                20                  25                  30 cct gga act tca gtg aag ata tcc tgc aag gct tct ggt tat tca ttc    144
Pro Gly Thr Ser Val Lys Ile Ser Cys Lys Ala Ser Gly Tyr Ser Phe
            35                  40                  45 act ggc ttc acc atg aac tgg gtg aag cag agc cat gga aag aac ctt    192
Thr Gly Phe Thr Met Asn Trp Val Lys Gln Ser His Gly Lys Asn Leu
        50                  55                  60 gag tgg ttt gga ctt att aat cct ttc aat ggt aat act ggc tac aac    240
Glu Trp Phe Gly Leu Ile Asn Pro Phe Asn Gly Asn Thr Gly Tyr Asn
65                  70                  75                  80 cag aag ttc aag ggc aag gcc aca tta act gta gac aag tct tcc agc    288
Gln Lys Phe Lys Gly Lys Ala Thr Leu Thr Val Asp Lys Ser Ser Ser
                85                  90                  95 aca gcc ttc atg gag ctc ctc agt ctg aca tct gag gac tct gca gtc    336
Thr Ala Phe Met Glu Leu Leu Ser Leu Thr Ser Glu Asp Ser Ala Val
            100                 105                 110 tat tac tgt gca aga tcg gga aaa tcc tat gat tac gag gcc tgg ttt    384
Tyr Tyr Cys Ala Arg Ser Gly Lys Ser Tyr Asp Tyr Glu Ala Trp Phe
        115                 120                 125 act tac tgg ggc caa ggg act ctg gtc act gtc tct gca                423
Thr Tyr Trp Gly Gln Gly Thr Leu Val Thr Val Ser Ala
    130                 135                 140

<210> SEQ ID NO 5
<211> LENGTH: 141
<212> TYPE: PRT
<213> ORGANISM: Mus musculus
<220> FEATURE:
<221> NAME/KEY: misc_feature
<222> LOCATION: (1)...(141)
<223> OTHER INFORMATION: heavy chain V segment of IgH-VJ558 family

<400> SEQUENCE: 5

```
Met Gly Trp Ser Trp Ile Phe Leu Phe Leu Leu Ser Gly Thr Ala Gly
 1               5                  10                  15

Val His Ser Glu Val Gln Leu Gln Gln Ser Gly Pro Glu Leu Val Lys
                 20                  25                  30

Pro Gly Thr Ser Val Lys Ile Ser Cys Lys Ala Ser Gly Tyr Ser Phe
             35                  40                  45

Thr Gly Phe Thr Met Asn Trp Val Lys Gln Ser His Gly Lys Asn Leu
         50                  55                  60

Glu Trp Phe Gly Leu Ile Asn Pro Phe Asn Gly Asn Thr Gly Tyr Asn
 65                  70                  75                  80

Gln Lys Phe Lys Gly Lys Ala Thr Leu Thr Val Asp Lys Ser Ser Ser
                 85                  90                  95

Thr Ala Phe Met Glu Leu Leu Ser Leu Thr Ser Glu Asp Ser Ala Val
            100                 105                 110

Tyr Tyr Cys Ala Arg Ser Gly Lys Ser Tyr Asp Tyr Glu Ala Trp Phe
            115                 120                 125

Thr Tyr Trp Gly Gln Gly Thr Leu Val Thr Val Ser Ala
        130                 135                 140

<210> SEQ ID NO 6
<211> LENGTH: 340
<212> TYPE: DNA
<213> ORGANISM: Mus musculus
<220> FEATURE:
<221> NAME/KEY: misc_feature
<222> LOCATION: (1)...(340)
<223> OTHER INFORMATION: light chain V segment of Ig kappa V1 subgroup
<220> FEATURE:
<221> NAME/KEY: CDS
<222> LOCATION: (1)...(340)

<400> SEQUENCE: 6 gat att gtg atg aca caa act aca ctc tcc ctg cct gtc agt ctt gga      48
Asp Ile Val Met Thr Gln Thr Thr Leu Ser Leu Pro Val Ser Leu Gly
 1               5                  10                  15 aat caa gcc tcc atc tct tgc aga tct agt cag acc att gta cat act      96
Asn Gln Ala Ser Ile Ser Cys Arg Ser Ser Gln Thr Ile Val His Thr
                 20                  25                  30 aat gga aac acc tat tta gaa tgg tac ctg cag aaa cca ggc cag tct     144
Asn Gly Asn Thr Tyr Leu Glu Trp Tyr Leu Gln Lys Pro Gly Gln Ser
             35                  40                  45 cca aag ctc ctg att tac aaa gtt tcc aac cga ttt tct ggg gtc cca     192
Pro Lys Leu Leu Ile Tyr Lys Val Ser Asn Arg Phe Ser Gly Val Pro
         50                  55                  60 gac agg ttc agt ggc agt gga tca ggg aca gat ttc ata ctc aat atc     240
Asp Arg Phe Ser Gly Ser Gly Ser Gly Thr Asp Phe Ile Leu Asn Ile
 65                  70                  75                  80 agc aga gtg gag gct gag gat ctg gga gtt tat tac tgc ttt caa ggt     288
Ser Arg Val Glu Ala Glu Asp Leu Gly Val Tyr Tyr Cys Phe Gln Gly
                 85                  90                  95 tca cat gtt cca ttc acg ttc ggc tcg ggg aca aag ttg gaa ata aaa     336
Ser His Val Pro Phe Thr Phe Gly Ser Gly Thr Lys Leu Glu Ile Lys
            100                 105                 110 cgg a                                                               340
Arg

<210> SEQ ID NO 7
<211> LENGTH: 113
<212> TYPE: PRT
<213> ORGANISM: Mus musculus
```

```
<220> FEATURE:
<221> NAME/KEY: misc_feature
<222> LOCATION: (1)...(113)
<223> OTHER INFORMATION: light chain V segment of Ig kappa V1 subgroup

<400> SEQUENCE: 7
```

Asp Ile Val Met Thr Gln Thr Thr Leu Ser Leu Pro Val Ser Leu Gly
 1               5                  10                  15

Asn Gln Ala Ser Ile Ser Cys Arg Ser Ser Gln Thr Ile Val His Thr
             20                  25                  30

Asn Gly Asn Thr Tyr Leu Glu Trp Tyr Leu Gln Lys Pro Gly Gln Ser
         35                  40                  45

Pro Lys Leu Leu Ile Tyr Lys Val Ser Asn Arg Phe Ser Gly Val Pro
     50                  55                  60

Asp Arg Phe Ser Gly Ser Gly Ser Gly Thr Asp Phe Ile Leu Asn Ile
 65                  70                  75                  80

Ser Arg Val Glu Ala Glu Asp Leu Gly Val Tyr Tyr Cys Phe Gln Gly
                 85                  90                  95

Ser His Val Pro Phe Thr Phe Gly Ser Gly Thr Lys Leu Glu Ile Lys
             100                 105                 110

Arg

```
<210> SEQ ID NO 8
<211> LENGTH: 12
<212> TYPE: PRT
<213> ORGANISM: Artificial Sequence
<220> FEATURE:
<223> OTHER INFORMATION: respiratory syncytial virus

<400> SEQUENCE: 8
```

Ser Lys Pro Asn Asn Asp Phe His Phe Glu Val Phe
 1               5                  10

```
<210> SEQ ID NO 9
<211> LENGTH: 12
<212> TYPE: PRT
<213> ORGANISM: Artificial Sequence
<220> FEATURE:
<223> OTHER INFORMATION: respiratory syncytial virus

<400> SEQUENCE: 9
```

His Phe Glu Val Phe Asn Phe Val Pro Cys Ser Ile
 1               5                  10

```
<210> SEQ ID NO 10
<211> LENGTH: 7
<212> TYPE: PRT
<213> ORGANISM: Artificial Sequence
<220> FEATURE:
<223> OTHER INFORMATION: respiratory syncytial virus

<400> SEQUENCE: 10
```

Glu Val Phe Asn Phe Val Pro
 1               5

```
<210> SEQ ID NO 11
<211> LENGTH: 5
<212> TYPE: PRT
<213> ORGANISM: Artificial Sequence
<220> FEATURE:
<223> OTHER INFORMATION: respiratory syncytial virus

<400> SEQUENCE: 11
```

```
His Phe Glu Val Phe
 1               5

<210> SEQ ID NO 12
<211> LENGTH: 11
<212> TYPE: PRT
<213> ORGANISM: Artificial Sequence
<220> FEATURE:
<223> OTHER INFORMATION: respiratory syncytial virus

<400> SEQUENCE: 12

Asp Phe His Phe Glu Val Phe Asn Phe Val Pro
 1               5                  10

<210> SEQ ID NO 13
<211> LENGTH: 10
<212> TYPE: PRT
<213> ORGANISM: Artificial Sequence
<220> FEATURE:
<223> OTHER INFORMATION: respiratory syncytial virus

<400> SEQUENCE: 13

Asn Asn Asp Phe His Phe Glu Val Phe Asn
 1               5                  10

<210> SEQ ID NO 14
<211> LENGTH: 7
<212> TYPE: PRT
<213> ORGANISM: Artificial Sequence
<220> FEATURE:
<223> OTHER INFORMATION: respiratory syncytial virus

<400> SEQUENCE: 14

Phe Glu Val Phe Asn Phe Val
 1               5

<210> SEQ ID NO 15
<211> LENGTH: 10
<212> TYPE: PRT
<213> ORGANISM: Artificial Sequence
<220> FEATURE:
<223> OTHER INFORMATION: respiratory syncytial virus

<400> SEQUENCE: 15

Asn Asp Phe His Phe Glu Val Phe Asn Phe
 1               5                  10

<210> SEQ ID NO 16
<211> LENGTH: 32
<212> TYPE: PRT
<213> ORGANISM: Artificial Sequence
<220> FEATURE:
<223> OTHER INFORMATION: respiratory syncytial virus A2 strain
<220> FEATURE:
<221> NAME/KEY: ACETYLATION
<222> LOCATION: 1
<223> OTHER INFORMATION: acetylated lysine
<220> FEATURE:
<221> NAME/KEY: AMIDATION
<222> LOCATION: 32
<223> OTHER INFORMATION: amide modified isoleucine

<400> SEQUENCE: 16

Lys Pro Asn Asn Asp Phe His Phe Glu Val Phe Asn Phe Val Pro Cys
 1               5                  10                  15

Ser Ile Cys Ser Asn Asn Pro Thr Cys Trp Ala Ile Cys Lys Arg Ile
             20                  25                  30
```

```
<210> SEQ ID NO 17
<211> LENGTH: 12
<212> TYPE: PRT
<213> ORGANISM: Artificial Sequence
<220> FEATURE:
<223> OTHER INFORMATION: respiratory syncytial virus A2 strain

<400> SEQUENCE: 17

Lys Pro Asn Asn Asp Phe His Phe Glu Val Phe Asn
1               5                   10

<210> SEQ ID NO 18
<211> LENGTH: 12
<212> TYPE: PRT
<213> ORGANISM: Artificial Sequence
<220> FEATURE:
<223> OTHER INFORMATION: respiratory syncytial virus A2 strain

<400> SEQUENCE: 18

Pro Asn Asn Asp Phe His Phe Glu Val Phe Asn Phe
1               5                   10

<210> SEQ ID NO 19
<211> LENGTH: 12
<212> TYPE: PRT
<213> ORGANISM: Artificial Sequence
<220> FEATURE:
<223> OTHER INFORMATION: respiratory syncytial virus A2 strain

<400> SEQUENCE: 19

Asn Asn Asp Phe His Phe Glu Val Phe Asn Phe Val
1               5                   10

<210> SEQ ID NO 20
<211> LENGTH: 12
<212> TYPE: PRT
<213> ORGANISM: Artificial Sequence
<220> FEATURE:
<223> OTHER INFORMATION: respiratory syncytial virus A2 strain

<400> SEQUENCE: 20

Asn Asp Phe His Phe Glu Val Phe Asn Phe Val Pro
1               5                   10

<210> SEQ ID NO 21
<211> LENGTH: 12
<212> TYPE: PRT
<213> ORGANISM: Artificial Sequence
<220> FEATURE:
<223> OTHER INFORMATION: respiratory syncytial virus A2 strain

<400> SEQUENCE: 21

Asp Phe His Phe Glu Val Phe Asn Phe Val Pro Ser
1               5                   10

<210> SEQ ID NO 22
<211> LENGTH: 12
<212> TYPE: PRT
<213> ORGANISM: Artificial Sequence
<220> FEATURE:
<223> OTHER INFORMATION: respiratory syncytial virus A2 strain

<400> SEQUENCE: 22

Phe His Phe Glu Val Phe Asn Phe Val Pro Ser Ser
1               5                   10
```

```
<210> SEQ ID NO 23
<211> LENGTH: 12
<212> TYPE: PRT
<213> ORGANISM: Artificial Sequence
<220> FEATURE:
<223> OTHER INFORMATION: respiratory syncytial virus A2 strain

<400> SEQUENCE: 23

His Phe Glu Val Phe Asn Phe Val Pro Ser Ser Ile
 1               5                  10

<210> SEQ ID NO 24
<211> LENGTH: 50
<212> TYPE: PRT
<213> ORGANISM: Artificial Sequence
<220> FEATURE:
<223> OTHER INFORMATION: respiratory syncytial virus A2 strain

<400> SEQUENCE: 24

Arg Gln Asn Lys Pro Pro Asn Lys Pro Asn Asn Asp Phe His Phe Glu
 1               5                  10                  15

Val Phe Asn Phe Val Pro Cys Ser Ile Cys Ser Asn Asn Pro Thr Cys
            20                  25                  30

Trp Ala Ile Cys Lys Arg Ile Pro Asn Lys Lys Pro Gly Lys Lys Thr
        35                  40                  45

Thr Thr
    50

<210> SEQ ID NO 25
<211> LENGTH: 50
<212> TYPE: PRT
<213> ORGANISM: Artificial Sequence
<220> FEATURE:
<223> OTHER INFORMATION: respiratory syncytial virus A2 strain

<400> SEQUENCE: 25

Arg Gln Asn Lys Pro Pro Ser Lys Pro Asn Asn Asp Phe His Phe Glu
 1               5                  10                  15

Val Phe Asn Phe Val Pro Cys Ser Ile Cys Ser Asn Asn Pro Thr Cys
            20                  25                  30

Trp Ala Ile Cys Lys Arg Ile Pro Asn Lys Lys Pro Gly Lys Arg Thr
        35                  40                  45

Thr Thr
    50

<210> SEQ ID NO 26
<211> LENGTH: 50
<212> TYPE: PRT
<213> ORGANISM: Artificial Sequence
<220> FEATURE:
<223> OTHER INFORMATION: respiratory syncytial virus A2 strain

<400> SEQUENCE: 26

Arg Gln Asn Lys Pro Pro Ser Lys Pro Asn Asn Asp Phe His Phe Glu
 1               5                  10                  15

Val Phe Asn Phe Val Pro Cys Ser Ile Cys Ser Asn Asn Pro Thr Cys
            20                  25                  30

Trp Ala Ile Cys Lys Arg Ile Pro Asn Lys Lys Pro Gly Lys Lys Thr
        35                  40                  45

Thr Thr
    50
```

<210> SEQ ID NO 27
<211> LENGTH: 50
<212> TYPE: PRT
<213> ORGANISM: Artificial Sequence
<220> FEATURE:
<223> OTHER INFORMATION: respiratory syncytial virus A2 strain

<400> SEQUENCE: 27

Arg Ser Lys Asn Pro Pro Lys Lys Pro Lys Asp Asp Tyr His Phe Glu
1               5                   10                  15

Val Phe Asn Phe Val Pro Cys Ser Ile Cys Gly Asn Asn Gln Leu Cys
            20                  25                  30

Lys Ser Ile Cys Lys Thr Ile Pro Ser Asn Lys Pro Lys Lys Lys Pro
        35                  40                  45

Thr Ile
    50

<210> SEQ ID NO 28
<211> LENGTH: 127
<212> TYPE: PRT
<213> ORGANISM: Homo sapiens
<220> FEATURE:
<221> NAME/KEY: CHAIN
<222> LOCATION: (1)...(127)
<223> OTHER INFORMATION: heavy chain of respiratory syncytial
      virus antibody

<400> SEQUENCE: 28

Gln Val Gln Leu Val Gln Ser Glu Ser Glu Val Lys Lys Pro Gly Ala
1               5                   10                  15

Ser Val Thr Val Ser Cys Lys Pro Ser Gly Tyr Thr Phe Asn Thr Tyr
            20                  25                  30

Tyr Ile His Trp Val Arg Gln Ala Pro Gly Gln Gly Leu Glu Trp Met
        35                  40                  45

Gly Val Ile Asn Pro Ser Gly Gly Ser Thr Tyr Thr Gln Arg Phe
    50                  55                  60

Gln Asp Arg Val Thr Met Thr Thr Asp Thr Ser Thr Asn Thr Ile Tyr
65                  70                  75                  80

Met Asp Leu Thr Ser Leu Arg Ser Asp Asp Thr Ala Met Tyr Tyr Cys
            85                  90                  95

Val Arg Gly Ser Asn Leu Leu Pro His Leu Trp Glu Trp Lys Pro Ser
            100                 105                 110

His Phe Asp Ser Trp Gly Gln Gly Thr Leu Val Thr Val Ser Ser
        115                 120                 125

<210> SEQ ID NO 29
<211> LENGTH: 126
<212> TYPE: PRT
<213> ORGANISM: Homo sapiens
<220> FEATURE:
<221> NAME/KEY: CHAIN
<222> LOCATION: (1)...(126)
<223> OTHER INFORMATION: heavy chain of respiratory syncytial
      virus antibody

<400> SEQUENCE: 29

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Asn Tyr Tyr Trp Gly Trp Ile Arg Gln Pro Pro Gly Lys Gly Leu Glu
        35                  40                  45

```
Trp Ile Ala Ser Ile His Asp Ser Gly Ser Ile Tyr Tyr Asn Pro Ser
        50                  55                  60

Leu Arg Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Leu Val Trp Phe Gly Glu Leu Arg Asn Asn Trp Phe
                100                 105                 110

Asp Pro Trp Gly Gln Gly Thr Leu Val Thr Val Ala Ser Ala
                115                 120                 125

<210> SEQ ID NO 30
<211> LENGTH: 124
<212> TYPE: PRT
<213> ORGANISM: Homo sapiens
<220> FEATURE:
<221> NAME/KEY: CHAIN
<222> LOCATION: (1)...(124)
<223> OTHER INFORMATION: heavy chain of respiratory syncytial
      virus antibody

<400> SEQUENCE: 30

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Thr Ser Gly
                20                  25                  30

Gln Tyr Tyr Trp Ala Trp Ile Arg Gln Ala Pro Gly Lys Gly Leu Glu
                35                  40                  45

Trp Ile Gly Ser Ile His Tyr Ser Gly Ser Thr Tyr Gln Asn Pro Ser
        50                  55                  60

Leu Lys Ser Arg Leu Thr Ile Ser Val Asp Thr Ser Arg Asp Gln Ile
65                  70                  75                  80

Ser Met Lys Leu Ser Ser Val Thr Val Ala Glu Ser Ala Val Tyr Tyr
                85                  90                  95

Cys Ala Arg Gln Gln Leu Ser Leu Ser Pro Val Glu Asn Trp Phe Asp
                100                 105                 110

Pro Trp Gly Gln Gly Thr Leu Val Thr Val Ser Ser
                115                 120

<210> SEQ ID NO 31
<211> LENGTH: 124
<212> TYPE: PRT
<213> ORGANISM: Homo sapiens
<220> FEATURE:
<221> NAME/KEY: CHAIN
<222> LOCATION: (1)...(124)
<223> OTHER INFORMATION: heavy chain of respiratory syncytial
      virus antibody

<400> SEQUENCE: 31

Glu Glu Gln Leu Val Glu Ser Gly Gly Gly Leu Val Gln Pro Gly Arg
1               5                   10                  15

Ser Leu Arg Leu Ser Cys Val Gly Ser Gly Leu Arg Phe Glu Glu His
                20                  25                  30

Ala Met His Trp Val Arg Gln Ala Pro Gly Arg Gly Leu Glu Trp Val
                35                  40                  45

Ser Gly Ile Ser Trp Asn Ser Gly Ser Val Gly Tyr Ala Asp Ser Val
        50                  55                  60

Lys Gly Arg Phe Thr Thr Ser Arg Asp Asn Ala Lys Asp Ile Leu Phe
```

```
                65                  70                  75                  80
Leu Glu Met Asn Thr Leu Arg Ser Glu Asp Thr Ala Leu Tyr Phe Cys
                            85                  90                  95

Ala Ile Met Val Ala Thr Thr Lys Asn Asp Phe His Tyr Tyr Lys Asp
                100                 105                 110

Val Trp Gly Lys Gly Thr Thr Val Thr Val Ser Ser
            115                 120
```

<210> SEQ ID NO 32
<211> LENGTH: 124
<212> TYPE: PRT
<213> ORGANISM: Homo sapiens
<220> FEATURE:
<221> NAME/KEY: CHAIN
<222> LOCATION: (1)...(124)
<223> OTHER INFORMATION: heavy chain of respiratory syncytial
      virus antibody

<400> SEQUENCE: 32

```
Gln Val His Leu Val Gln Ser Gly Val Glu Val Lys Lys Pro Gly Ala
  1               5                  10                  15

Ser Val Arg Val Ser Cys Lys Ala Ser Gly Tyr Thr Phe Ala Thr Tyr
                20                  25                  30

Gly Ile Thr Trp Val Arg Gln Ala Pro Gly Arg Gly Leu Glu Trp Val
            35                  40                  45

Gly Trp Ile Thr Pro Tyr Asn Asp Arg Thr Ser Tyr Ala Gln Ile Phe
         50                  55                  60

His Gly Arg Val Thr Met Thr Thr Asp Thr Ser Thr Asn Thr Ala Tyr
 65                  70                  75                  80

Met Glu Leu Arg Ser Leu Arg Ser Asp Asp Thr Ala Met Tyr Tyr Cys
                85                  90                  95

Ala Arg Asn His Cys Asn Phe Tyr His Asp Phe Trp Ser Gly Leu Asp
                100                 105                 110

Tyr Trp Gly Gln Gly Thr Leu Val Ser Val Ser Ser
            115                 120
```

<210> SEQ ID NO 33
<211> LENGTH: 121
<212> TYPE: PRT
<213> ORGANISM: Homo sapiens
<220> FEATURE:
<221> NAME/KEY: CHAIN
<222> LOCATION: (1)...(121)
<223> OTHER INFORMATION: heavy chain of respiratory syncytial
      virus antibody

<400> SEQUENCE: 33

```
Gln Val Gln Leu Val Gln Ser Gly Ala Glu Val Lys Lys Pro Gly Ser
  1               5                  10                  15

Ser Val Lys Val Pro Cys Lys Ala Ser Gly Gly Thr Phe Ser Thr Tyr
                20                  25                  30

Pro Ile Ser Trp Val Arg Gln Ala Pro Gly Gln Gly Leu Glu Trp Met
            35                  40                  45

Gly Arg Ile Ile Pro Asp Pro Pro Met Ala Asn Ile Ala Gln Lys Phe
         50                  55                  60

Gln Gly Arg Val Ser Phe Ser Ala Asp Lys Ser Thr Thr Ile Val Tyr
 65                  70                  75                  80

Met Glu Leu Ser Ser Leu Arg Ser Glu Asp Thr Ala Val Tyr Phe Cys
                85                  90                  95
```

```
Ala Arg Glu Ile Leu Gln Ser Pro Pro Phe Ala Val Asp Val Trp Gly
            100                 105                 110
Gln Gly Thr Met Val Ala Val Ser Ser
        115                 120
```

<210> SEQ ID NO 34
<211> LENGTH: 127
<212> TYPE: PRT
<213> ORGANISM: Homo sapiens
<220> FEATURE:
<221> NAME/KEY: CHAIN
<222> LOCATION: (1)...(127)
<223> OTHER INFORMATION: heavy chain of respiratory syncytial
      virus antibody

<400> SEQUENCE: 34

```
Gln Ala Gln Leu Val Glu Ser Gly Gly Val Val Gln Pro Gly Arg
  1               5                  10                  15
Ser Leu Arg Leu Ser Cys Ala Ala Ser Gly Phe Thr Phe Ser Tyr Ser
             20                  25                  30
Gly Met His Trp Val Arg Gln Ala Pro Gly Arg Gly Leu Glu Trp Leu
         35                  40                  45
Ala Val Ile Ser Tyr Asp Gly Asn Lys Met Tyr Tyr Ala Asp Ser Val
     50                  55                  60
Lys Gly Arg Phe Thr Ile Ser Arg Asp Asn Ser Lys Met Thr Leu Tyr
 65                  70                  75                  80
Leu Gln Met Asn Ser Leu Arg Arg Glu Asp Thr Ala Val Tyr Tyr Cys
                 85                  90                  95
Ala Lys Asp Gly Leu Asp Tyr Gly Gly Asp Leu Val Tyr Gly Met
            100                 105                 110
Asp Val Trp Gly Asn Gly Thr Thr Val Thr Val Ser Ser Ala Ser
            115                 120                 125
```

<210> SEQ ID NO 35
<211> LENGTH: 126
<212> TYPE: PRT
<213> ORGANISM: Homo sapiens
<220> FEATURE:
<221> NAME/KEY: CHAIN
<222> LOCATION: (1)...(126)
<223> OTHER INFORMATION: heavy chain of respiratory syncytial
      virus antibody

<400> SEQUENCE: 35

```
Gln Val Gln Leu Val Gln Ser Gly Pro Glu Val Lys Lys Pro Gly Ala
  1               5                  10                  15
Ser Val Arg Leu Ser Cys Lys Ala Ser Gly Tyr Val Phe Thr Asn Tyr
             20                  25                  30
Gly Val Ser Trp Val Arg Gln Ala Pro Gly Gln Gly Leu Glu Trp Met
         35                  40                  45
Gly Trp Ser Ser Pro Tyr Asn Gly Asn Thr Tyr Tyr Ala Gln Lys Leu
     50                  55                  60
Lys Ala Arg Val Thr Met Thr Thr Asp Thr Ser Thr Asn Thr Ala Tyr
 65                  70                  75                  80
Met Glu Leu Arg Ser Leu Arg Ser Asp Asp Thr Ala Val Tyr Tyr Cys
                 85                  90                  95
Gly Arg Asp Met Leu Gly Val Val Gln Ala Val Ala Gly Pro Phe Asp
            100                 105                 110
Ser Trp Gly Gln Gly Thr Leu Val Thr Val Ser Ser Ala Ser
            115                 120                 125
```

<210> SEQ ID NO 36
<211> LENGTH: 126
<212> TYPE: PRT
<213> ORGANISM: Homo sapiens
<220> FEATURE:
<221> NAME/KEY: CHAIN
<222> LOCATION: (1)...(126)
<223> OTHER INFORMATION: heavy chain of respiratory syncytial virus antibody

<400> SEQUENCE: 36

Gln Val Gln Leu Val Gln Ser Gly Gly Glu Val Lys Arg Pro Gly Ala
1               5                   10                  15
Ser Val Arg Val Ser Cys Lys Ala Ser Gly Tyr Thr Phe Ile Asn Tyr
            20                  25                  30
Ala Ile Ser Trp Val Arg Gln Ala Pro Gly Gln Gly Leu Glu Trp Leu
        35                  40                  45
Gly Trp Ile Ser Ala Tyr Asn Gly Asn Thr His Tyr Ala Gln Lys Val
    50                  55                  60
Gln Asp Arg Val Thr Met Thr Thr Asp Ala Ser Thr Thr Thr Ala Tyr
65                  70                  75                  80
Met Glu Leu Arg Gly Leu Lys Ser Asp Asp Thr Ala Val Tyr Ser Cys
                85                  90                  95
Ala Arg Leu Pro Leu Leu Gly Tyr Ser Ser Gly Trp Tyr Ala Phe Asp
            100                 105                 110
Met Trp Arg Gln Gly Thr Met Val Pro Val Ser Ser Ala Ser
        115                 120                 125

<210> SEQ ID NO 37
<211> LENGTH: 127
<212> TYPE: PRT
<213> ORGANISM: Homo sapiens
<220> FEATURE:
<221> NAME/KEY: CHAIN
<222> LOCATION: (1)...(127)
<223> OTHER INFORMATION: heavy chain of respiratory syncytial virus antibody

<400> SEQUENCE: 37

Gln Val Gln Leu Leu Gln Ser Gly Ala Glu Leu Lys Lys Pro Gly Ala
1               5                   10                  15
Ser Val Lys Val Ser Cys Gln Ala Ser Ile Asp Thr Phe Ser Thr Tyr
            20                  25                  30
Tyr Ile His Trp Val Arg Gln Ala Pro Gly Gln Gly Leu Glu Trp Leu
        35                  40                  45
Gly Val Ile Asn Pro Ser Gly Gly Ser Thr Thr Tyr Ala Gln Lys Phe
    50                  55                  60
Gln Asp Arg Ile Thr Leu Thr Thr Asp Thr Ser Thr Arg Thr Val Tyr
65                  70                  75                  80
Met Asp Leu Ser Ser Leu Arg Ser Glu Asp Thr Ala Val Tyr Tyr Cys
                85                  90                  95
Ala Arg Val His Lys Gly Arg Ala Glu Gln Trp Gln Leu Leu His Gly
            100                 105                 110
His Phe Asp Leu Trp Gly Arg Gly Ser Leu Val Thr Val Ser Ser
        115                 120                 125

<210> SEQ ID NO 38
<211> LENGTH: 126
<212> TYPE: PRT

<213> ORGANISM: Homo sapiens
<220> FEATURE:
<221> NAME/KEY: CHAIN
<222> LOCATION: (1)...(126)
<223> OTHER INFORMATION: heavy chain of respiratory syncytial
      virus antibody

<400> SEQUENCE: 38

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Thr Ser Gly
            20                  25                  30

Gln Tyr Tyr Trp Ala Trp Ile Arg Gln Ala Pro Gly Lys Gly Leu Glu
        35                  40                  45

Trp Ile Gly Ser Ile His Tyr Ser Gly Ser Thr Tyr Gln Asn Pro Ser
    50                  55                  60

Leu Lys Ser Arg Leu Thr Ile Ser Val Asp Thr Ser Arg Asp Gln Ile
65                  70                  75                  80

Ser Met Lys Leu Ser Ser Val Thr Val Ala Glu Ser Ala Val Tyr Tyr
                85                  90                  95

Cys Ala Lys Gln Gln Leu Ser Leu Ser Pro Val Glu Asn Trp Phe Asp
            100                 105                 110

Pro Trp Gly Gln Gly Thr Leu Val Thr Val Ser Ser Ala Ser
        115                 120                 125

<210> SEQ ID NO 39
<211> LENGTH: 120
<212> TYPE: PRT
<213> ORGANISM: Homo sapiens
<220> FEATURE:
<221> NAME/KEY: CHAIN
<222> LOCATION: (1)...(120)
<223> OTHER INFORMATION: heavy chain of respiratory syncytial
      virus antibody

<400> SEQUENCE: 39

Glu Val Gln Val Val Glu Ser Gly Gly Gly Leu Val Gln Pro Gly Gly
1               5                   10                  15

Ser Leu Arg Leu Ser Cys Val Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Tyr Ser Asp Gly Ser Ser Thr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Val Leu Gly Ala Ala Met Phe Asp Ile Trp Gly Gln Gly Thr
            100                 105                 110

Val Val Thr Val Ser Ser Ala Ser
        115                 120

<210> SEQ ID NO 40
<211> LENGTH: 128
<212> TYPE: PRT
<213> ORGANISM: Homo sapiens
<220> FEATURE:
<221> NAME/KEY: CHAIN
<222> LOCATION: (1)...(128)
<223> OTHER INFORMATION: heavy chain of respiratory syncytial virus antibody

<400> SEQUENCE: 40

```
Gln Val Gln Leu Val Glu Ser Gly Gly Gly Val Val Gln Pro Gly Arg
1               5                   10                  15

Ser Leu Arg Leu Ser Cys Glu Ala Ser Gly Phe Thr Phe Ser Gly Tyr
            20                  25                  30

Ala Met His Trp Val Arg Gln Ala Pro Ala Lys Gly Leu Glu Trp Val
        35                  40                  45

Ala Val Ile Ser Phe Asp Gly Ser Asn Asn Tyr Tyr Ala Asp Ser Val
    50                  55                  60

Lys Gly Arg Phe Thr Ile Ser Arg Asp Asn Ser Lys Asn Met Leu Phe
65                  70                  75                  80

Leu Gln Met Asn Ser Leu Arg Ala Glu Asp Thr Ala Val Tyr Tyr Cys
                85                  90                  95

Val Arg Pro Asp Val Ile Ala Val Ala Gly Thr Ala Leu Ser Asn Pro
            100                 105                 110

Phe Asp Leu Trp Gly Leu Gly Thr Met Val Thr Val Ser Ser Ala Ser
        115                 120                 125
```

<210> SEQ ID NO 41
<211> LENGTH: 122
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(122)
<223> OTHER INFORMATION: humanized heavy chain of respiratory syncytial virus antibody

<400> SEQUENCE: 41

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Phe
            20                  25                  30

Thr Met Asn Trp Val Arg Gln Ala Thr Gly Gln Gly Leu Glu Trp Met
        35                  40                  45

Gly Leu Ile Asn Pro Phe Asn Gly Asn Thr Gly Tyr Asn Gln Lys Phe
    50                  55                  60

Lys Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Lys Ser Tyr Asp Tyr Glu Ala Trp Phe Thr Tyr Trp
            100                 105                 110

Gly Gln Gly Thr Leu Val Thr Val Ser Ala
        115                 120
```

<210> SEQ ID NO 42
<211> LENGTH: 109
<212> TYPE: PRT
<213> ORGANISM: Homo sapiens
<220> FEATURE:
<221> NAME/KEY: CHAIN
<222> LOCATION: (1)...(109)
<223> OTHER INFORMATION: light chain of respiratory syncytial virus antibody

<400> SEQUENCE: 42

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Ile Thr Asn Asn
                20                  25                  30

Tyr Leu Ala Trp Tyr Gln Gln Lys Pro Gly Gln Ala Pro Arg Leu Leu
            35                  40                  45

Ile Tyr Asp Ser Phe Ser Arg Ala Thr Gly Ile Pro Glu Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Val Arg Ser Pro
                85                  90                  95

Leu Thr Phe Gly Pro Gly Thr Lys Val Glu Ile Lys Arg
                100                 105
```

<210> SEQ ID NO 43
<211> LENGTH: 107
<212> TYPE: PRT
<213> ORGANISM: Homo sapiens
<220> FEATURE:
<221> NAME/KEY: CHAIN
<222> LOCATION: (1)...(107)
<223> OTHER INFORMATION: light chain of respiratory syncytial
      virus antibody

<400> SEQUENCE: 43

```
Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Asn Ser Asn
                20                  25                  30

Leu Ala Trp Tyr Gln His Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
        50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Phe Gly Pro Gly Thr Lys Val Asp Leu Lys Arg
                100                 105
```

<210> SEQ ID NO 44
<211> LENGTH: 109
<212> TYPE: PRT
<213> ORGANISM: Homo sapiens
<220> FEATURE:
<221> NAME/KEY: CHAIN
<222> LOCATION: (1)...(109)
<223> OTHER INFORMATION: light chain of respiratory syncytial
      virus antibody

<400> SEQUENCE: 44

```
Glu Ile Val Val Thr Gln Ser Pro Val Thr Leu Ser Val Ser Pro Gly
 1               5                  10                  15

Glu Ser Ala Thr Leu Ser Cys Arg Ser Ala Arg Ser Val Gly Ser Arg
                20                  25                  30

Leu Ala Trp Tyr Gln Gln Lys Pro Gly Gln Pro Pro Arg Leu Leu Ile
            35                  40                  45

Phe Ala Ala Ser Thr Arg Ala Thr Gly Ile Pro Ala Arg Phe Ser Gly
```

```
                        50                  55                  60
Ser Gly Ser Gly Thr Asp Phe Thr Leu Ile Ile Ser Gly Leu Gln Ser
 65                  70                  75                  80

Glu Asp Tyr Ala Val Tyr Tyr Cys Gln Gln Tyr Lys Glu Trp Pro Leu
                 85                  90                  95

Phe Thr Phe Gly Pro Gly Thr Val Asp Ser Lys Arg
            100                 105
```

<210> SEQ ID NO 45
<211> LENGTH: 106
<212> TYPE: PRT
<213> ORGANISM: Homo sapiens
<220> FEATURE:
<221> NAME/KEY: CHAIN
<222> LOCATION: (1)...(106)
<223> OTHER INFORMATION: light chain of respiratory syncytial
      virus antibody

<400> SEQUENCE: 45

```
Gln Ile Val Leu Thr Gln Ser Pro Ala Thr Leu Ser Leu Ser Pro Gly
 1               5                  10                  15

Glu Arg Ala Thr Leu Ser Cys Lys Ala Ser Gln Ser Val Ser Asn His
                20                  25                  30

Leu Ala Trp Tyr Gln Gln Lys Pro Gly Gln Ala Pro Arg Leu Leu Ile
            35                  40                  45

Tyr Glu Thr Ser Asn Arg Ala Thr Gly Ile Pro Pro Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Asn Asn Trp Tyr Thr
                 85                  90                  95

Phe Gly Gln Gly Thr Lys Leu Glu Ile Lys
            100                 105
```

<210> SEQ ID NO 46
<211> LENGTH: 108
<212> TYPE: PRT
<213> ORGANISM: Homo sapiens
<220> FEATURE:
<221> NAME/KEY: CHAIN
<222> LOCATION: (1)...(108)
<223> OTHER INFORMATION: light chain of respiratory syncytial
      virus antibody

<400> SEQUENCE: 46

```
Ser Phe Glu Leu Thr Gln Pro Pro Ser Val Ser Val Ser Pro Gly Gln
 1               5                  10                  15

Thr Ala Arg Ile Thr Cys Ser Gly Asp Ala Leu Pro Lys Gln Tyr Val
                20                  25                  30

Tyr Trp Tyr Gln Gln Lys Pro Gly Gln Ala Pro Val Leu Val Ile Tyr
            35                  40                  45

Lys Thr Thr Glu Arg Pro Ser Gly Ile Pro Glu Arg Phe Ser Asp Ser
 50                  55                  60

Ser Ser Gly Thr Thr Val Thr Leu Thr Ile Ser Ala Ala Gln Ala Glu
 65                  70                  75                  80

Asp Glu Ala Asp Tyr Tyr Cys Gln Ser Val Asp Ser Ser Gly Thr Tyr
                 85                  90                  95

Val Phe Gly Ile Gly Thr Lys Val Thr Val Leu Gly
            100                 105
```

```
<210> SEQ ID NO 47
<211> LENGTH: 113
<212> TYPE: PRT
<213> ORGANISM: Homo sapiens
<220> FEATURE:
<221> NAME/KEY: CHAIN
<222> LOCATION: (1)...(113)
<223> OTHER INFORMATION: light chain of respiratory syncytial
      virus antibody

<400> SEQUENCE: 47
```

Gln Ser Ala Leu Thr Gln Pro Ala Ser Val Ser Gly Ser Pro Gly Gln
1               5                   10                  15

Ser Ile Thr Ile Ser Cys Thr Gly Ser Ser Ser Asp Val Gly Gly Tyr
            20                  25                  30

Ser His Val Ser Trp Tyr Gln Gln His Pro Gly Lys Val Pro Lys Leu
        35                  40                  45

Ile Ile Ser Glu Val Ser Asn Arg Pro Ser Gly Ile Ser Asn Arg Phe
    50                  55                  60

Ser Gly Ser Lys Ser Ala Asn Thr Ala Ser Leu Thr Ile Ser Gly Leu
65                  70                  75                  80

Gln Pro Glu Asp Glu Ala Asp Tyr Tyr Cys Gly Ser Tyr Ala Ser Thr
                85                  90                  95

Asn Ile Leu His Tyr Val Phe Gly Thr Gly Thr Lys Val Thr Val Leu
            100                 105                 110

Ser

```
<210> SEQ ID NO 48
<211> LENGTH: 114
<212> TYPE: PRT
<213> ORGANISM: Homo sapiens
<220> FEATURE:
<221> NAME/KEY: CHAIN
<222> LOCATION: (1)...(114)
<223> OTHER INFORMATION: light chain of respiratory syncytial
      virus antibody

<400> SEQUENCE: 48
```

Ser Tyr Glu Leu Thr Gln Pro Pro Ser Val Ser Val Ser Pro Gly Gln
1               5                   10                  15

Thr Gly Arg Ile Thr Cys Thr Gly Ser Glu Ala Ser Gly Asp Ala Leu
            20                  25                  30

Ala Ser Arg Tyr Ala Tyr Trp Tyr Gln His Lys Ser Gly Gln Ala Pro
        35                  40                  45

Val Val Leu Ile Tyr Lys Asp Thr Glu Arg Pro Ser Gly Ile Ser Glu
    50                  55                  60

Arg Phe Ser Gly Ser Ser Ser Gly Thr Thr Val Thr Leu Ile Ile Ser
65                  70                  75                  80

Gly Val Leu Ala Glu Asp Glu Ala Asp Tyr Tyr Cys Lys Thr Ser Val
                85                  90                  95

Arg Asn Gly Thr Ser Trp Val Phe Gly Thr Gly Thr Met Leu Thr Val
            100                 105                 110

Leu Arg

```
<210> SEQ ID NO 49
<211> LENGTH: 108
<212> TYPE: PRT
<213> ORGANISM: Homo sapiens
<220> FEATURE:
<221> NAME/KEY: CHAIN
```

<222> LOCATION: (1)...(108)
<223> OTHER INFORMATION: light chain of respiratory syncytial
      virus antibody

<400> SEQUENCE: 49

Asp Thr Pro Met Thr Gln Ser Pro Ser Val Ser Ala Ser Val Gly
1               5                   10                  15

Asp Arg Val Thr Ile Ser Cys Arg Ala Ser Gln Gly Ile Ser Asn Ser
            20                  25                  30

Leu Ala Trp Tyr Gln Gln Lys Leu Gly Lys Ala Pro Gln Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Thr Phe Pro Phe
                85                  90                  95

Thr Phe Gly Pro Gly Thr Lys Val Glu Val Arg Arg
            100                 105

<210> SEQ ID NO 50
<211> LENGTH: 111
<212> TYPE: PRT
<213> ORGANISM: Homo sapiens
<220> FEATURE:
<221> NAME/KEY: CHAIN
<222> LOCATION: (1)...(111)
<223> OTHER INFORMATION: light chain of respiratory syncytial
      virus antibody

<400> SEQUENCE: 50

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Asn Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Glu Tyr Tyr Cys Ser Ser Tyr Ala Gly Ser
                85                  90                  95

Met Asn Trp Val Phe Gly Gly Gly Thr Lys Leu Thr Val Leu Gly
            100                 105                 110

<210> SEQ ID NO 51
<211> LENGTH: 114
<212> TYPE: PRT
<213> ORGANISM: Homo sapiens
<220> FEATURE:
<221> NAME/KEY: CHAIN
<222> LOCATION: (1)...(114)
<223> OTHER INFORMATION: light chain of respiratory syncytial
      virus antibody

<400> SEQUENCE: 51

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

```
Ser Asn Asn Lys Thr Tyr Leu Ala Trp Tyr Gln Gln Lys Pro Arg Gln
            35                  40                  45

Pro Pro Glu Leu Leu Ile Tyr Trp Ala Ser Thr Arg Glu Ser Gly Val
 50                  55                  60

Pro Asp Arg Phe Ser Gly Ser Gly Ser Gly Thr Asn Phe Thr Leu Thr
 65                  70                  75                  80

Ile Ser Ser Leu Gln Ala Glu Asp Val Ala Val Tyr Tyr Cys Gln Gln
                85                  90                  95

Tyr Tyr Thr Thr Pro Tyr Thr Phe Gly Gln Gly Thr Lys Leu Glu Ile
            100                 105                 110

Lys Arg

<210> SEQ ID NO 52
<211> LENGTH: 109
<212> TYPE: PRT
<213> ORGANISM: Homo sapiens
<220> FEATURE:
<221> NAME/KEY: CHAIN
<222> LOCATION: (1)...(109)
<223> OTHER INFORMATION: light chain of respiratory syncytial
      virus antibody

<400> SEQUENCE: 52

Glu Ile Val Val Thr Gln Ser Pro Val Thr Leu Ser Val Ser Pro Gly
 1                   5                  10                  15

Glu Ser Ala Ala Leu Ser Cys Arg Ala Ser Arg Ser Val Gly Ser Arg
                20                  25                  30

Leu Ala Trp Tyr Gln Gln Lys Pro Gly Gln Pro Arg Leu Leu Ile
            35                  40                  45

Phe Ala Ala Ser Thr Arg Ala Thr Gly Ile Pro Ala Arg Phe Ser Gly
 50                  55                  60

Ser Gly Ser Gly Thr Asp Phe Thr Leu Ile Ile Ser Gly Leu Gln Ser
 65                  70                  75                  80

Glu Asp Tyr Ala Val Tyr Tyr Cys Gln Gln Tyr Lys Glu Trp Pro Leu
                85                  90                  95

Phe Thr Phe Gly Pro Gly Thr Thr Val Asp Ser Lys Arg
            100                 105

<210> SEQ ID NO 53
<211> LENGTH: 110
<212> TYPE: PRT
<213> ORGANISM: Homo sapiens
<220> FEATURE:
<221> NAME/KEY: CHAIN
<222> LOCATION: (1)...(110)
<223> OTHER INFORMATION: light chain of respiratory syncytial
      virus antibody

<400> SEQUENCE: 53

Glu Ile Val Leu Thr Gln Ser Pro Ala Thr Leu Ser Leu Ser Pro Gly
 1                   5                  10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Ser Asp Ala Ser Asn Arg Ala Thr Gly Ile Pro Pro Arg Phe Ser Gly
 50                  55                  60

Ser Gly Ser Gly Thr Asp Phe Thr Leu Thr Ile Ser Ser Leu Glu Pro
 65                  70                  75                  80
```

```
Glu Asp Phe Ala Val Tyr Tyr Cys Gln Gln Arg Ser Asn Trp Pro Pro
                85                  90                  95
Arg Phe Thr Phe Gly Pro Gly Thr Ile Val Asp Ile Arg Arg
            100                 105                 110

<210> SEQ ID NO 54
<211> LENGTH: 107
<212> TYPE: PRT
<213> ORGANISM: Homo sapiens
<220> FEATURE:
<221> NAME/KEY: CHAIN
<222> LOCATION: (1)...(107)
<223> OTHER INFORMATION: light chain of respiratory syncytial
      virus antibody

<400> SEQUENCE: 54

Glu Ile Val Met Thr Gln Ser Pro Ala Thr Leu Ser Val Ser Pro Gly
 1               5                  10                  15

Glu Arg Ala Leu Ser Cys Arg Ala Ser Gln Ser Val Arg Ser Asn Leu
             20                  25                  30

Val Trp Tyr Gln Gln Lys Pro Gly Gln Ala Pro Arg Leu Leu Ile Phe
         35                  40                  45

Gly Ala Ser Thr Arg Ala Thr Gly Ile Pro Ala Arg Phe Ser Gly Ser
     50                  55                  60

Gly Ser Gly Thr Glu Phe Thr Leu Thr Ile Ser Ser Leu Gln Ser Glu
 65                  70                  75                  80

Asp Phe Ala Leu Tyr Phe Cys Gln Gln Asn Asn Asn Trp Pro Pro Thr
                85                  90                  95

Phe Gly Gln Gly Thr Arg Leu Glu Ile Lys Arg
            100                 105

<210> SEQ ID NO 55
<211> LENGTH: 113
<212> TYPE: PRT
<213> ORGANISM: Artificial Sequence Sequence
<220> FEATURE:
<223> OTHER INFORMATION: synthetic construct
<220> FEATURE:
<221> NAME/KEY: CHAIN
<222> LOCATION: (1)...(113)
<223> OTHER INFORMATION: humanized light chain of respiratory
      syncytial virus antibody

<400> SEQUENCE: 55

Asp Ile Val Met Thr Gln Thr Pro Leu Ser Leu Ser Val Thr Pro Gly
 1               5                  10                  15

Gln Pro Ala Ser Ile Ser Cys Arg Ser Ser Gln Thr Ile Val His Thr
             20                  25                  30

Asn Gly Asn Thr Tyr Leu Glu Trp Tyr Leu Gln Lys Pro Gly Gln Ser
         35                  40                  45

Pro Gln Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                85                  90                  95

Ser His Val Pro Phe Thr Phe Gly Ser Gly Thr Lys Leu Glu Ile Lys
            100                 105                 110

Arg
```

```
<210> SEQ ID NO 56
<211> LENGTH: 9
<212> TYPE: PRT
<213> ORGANISM: Artificial Sequence
<220> FEATURE:
<223> OTHER INFORMATION: respiratory syncytial virus A2 strain

<400> SEQUENCE: 56

His Phe Glu Val Phe Asn Phe Val Pro
 1               5
```

ANTI-RSV G PROTEIN ANTIBODIES

CROSS-REFERENCE TO RELATED APPLICATIONS

This application is a continuation of U.S. patent application Ser. No. 12/778,933, filed 12 May 2010, now allowed, which is a continuation of U.S. patent application Ser. No. 12/258,260, filed 24 Oct. 2008, now allowed, and claims priority from U.S. Provisional Applications 61/000,469 filed 25 Oct. 2007 and 61/089,401 filed 15 Aug. 2008. The contents of these documents are incorporated herein by reference.

CROSS-REFERENCE TO RELATED APPLICATIONS

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 677622011902Seqlist.txt | Sep. 25, 2012 | 45,468 bytes |

TECHNICAL FIELD

The invention is directed to antibodies that are immunoreactive with a functionally important epitope contained on the G protein from respiratory syncytial virus (RSV) that are minimally immunogenic when administered to a human subject. These antibodies may be used to increase resistance of human subjects against RSV infection as well as to diminish the level of infection in individuals already infected or to ameliorate the symptoms caused by RSV infection.

BACKGROUND ART

RSV infection has been a longstanding and pernicious problem globally, including the United States, Europe, Australia and Japan. It is particularly troublesome in premature infants, young children, and the elderly, and indeed for all individuals with a weakened immune system. It is estimated that about two thirds of children below age 1 and almost all children between age 1 and 4 are infected at least once with RSV, with most recovering without any need for medical attention. However, 5-10% have prolonged severe infection, a factor believed to be predisposing to wheezing and asthma-like symptoms later in childhood. RSV has two major surface glycoproteins, F and G. The sole marketed monoclonal antibody against RSV is only approved for prophylactic use in premature infants to prevent infection by RSV, and is directed against the F protein. This antibody, palivizumab (Synagis®, from Medlmmune) is broadly useful due to conservation of the F protein sequence among strains. By contrast, the G protein is quite variable except for a central "CX3C" domain that is nearly invariant in nearly 100 sequenced strains. This region includes a motif that has been shown to interact with the fractalkine receptor. That interaction is believed to contribute to the prolonged disease course characteristic of RSV by suppressing an effective immune response to the virus: Tripp, R. A, et al., *Nature Immunology* (2001) 2:732-738. This region has also been shown to be an antagonist of the Toll-like Receptor 4, which is again believed to contribute to suppressing an effective immune response: Polack, et al., *Proc. Natl. Acad. Sci. USA* (2005) 102:8996-9001; Shingai, et al., *Int'l Immunology* (2008) epub July 8.

Initial attempts at prophylaxis for RSV by vaccination proved counterproductive. Enhanced disease and pulmonary eosinophilia were associated with vaccination with formalin inactivated RSV or with RSV G glycoprotein and this has been attributed to the above noted conserved sequence in the G protein designated CX3C region which mimics the chemokine fractalkine. (Haynes, L. M., et al., *J. Virol.* (2003) 77:9831-9844.) Passive immunization using antibodies directed to the G protein has generally been considered impractical due to the lack of conservation of the sequence of this protein among strains.

It has subsequently been confirmed by the same group that anti-G protein antibody responses engendered by RSV infection or vaccination are associated with inhibition of the binding of the G protein to the fractalkine CX3C receptor and with modulation of RSV G-protein-mediated leukocyte chemotaxis (Harcourt, J. L., et al., *J. I. D.* (2004) 190:1936-1940) and that inhibition of this binding adversely affects T cell responses (Harcourt, J. L., et al., *J. Immunol.* (2006) 176: 1600-1608). More recent vaccine efforts have avoided the worsening of disease associated with the formalin fixed vaccine, but the immunity conferred by the newer vaccines has been found to wane rapidly (weeks to months), consistent with the poor immunological memory to natural RSV: Yu, et al., *J. Virol.* (2008) 82:2350-2357. Repeated infection is common for this virus, unlike many others. The immunosuppressive properties of the G protein may be responsible for this effect.

Monoclonal antibodies directed against the G protein have been known for over 20 years. Anderson, L. J., et al., *J. Virol.* (1988) 62:4232-4238 describe the ability of mixtures of F and G protein monoclonal antibodies (mAbs), and of the individual mAbs, to neutralize RSV. The mAbs relevant to binding G protein, notably 131-2G, were later studied by Sullender, W., *Virol.* (1995) 209:70-79 in an antigenic analysis. This antibody was found to bind both RSV groups A and B, representing the major strains of RSV.

In addition, Mekseepralard, C., et al., *J. Gen. Virol.* (2006) 87:1267-1273 summarize earlier papers showing that passively administered antibodies both to F and G protein were protective against experimental infection in rodent models. These articles include Routledge, et al., *J. Gen. Virol.* (1988) 69:293-303; Stott, E. J., et al., *J. Virol.* (1986) 60:607-613; Taylor, G., et al., *Immunol.* (1994) 52:137-142; and Walsh, E. E., et al., *Infect. Immun.* (1984) 43:756-758. In the instant article, Mekseepralard, et al., noted that a specific monoclonal antibody raised against the G protein (1C2) required glycosylation in order to neutralize the virus in the presence of complement in vitro or when used in vivo in mice. The authors note that amino acids 173-186 of the G protein are conserved and that 1C2 was directed against a conserved region; however, the method for preparing non-immunogenic antibodies was relatively crude, namely chimerization of a murine Fab onto a human Fc region.

In addition, Corbeil, S., et al., *Vaccine* (1996) 14:521-525 demonstrate that the complement system is involved in the protection of mice from challenge with RSV after passive immunization with the murine monoclonal antibody 18A2B2, even though this antibody does not show neutralizing capability in vitro.

PCT publication WO 00/43040 describes the use of anti-Substance P antibodies in ameliorating the airway inflammation associated with infection by RSV. The production of Substance P, a known proinflammatory mediator, is enhanced by administration of the G protein of RSV and is absent in mutants of RSV that are missing the G protein or carry a function defeating point mutation in the central conserved region: Haynes, et al., *J Virol* (2003) 77:9831-9844.

U.S. patent publication 2006/0018925 describes and claims antibodies and small peptides that are able to block the interaction of CX3C region of the G protein with its receptor. These compositions are suggested as useful for modulating RSV infection and inducing immunity. Although humanization of the murine antibodies employed in the demonstration of the therapeutic and prophylactic value of these antibodies is suggested, no such humanized forms were actually produced or described.

PCT publication WO2007/101441, assigned to Symphogen, is directed to recombinant polyclonal antibodies for treatment of RSV infections. The polyclonal recombinant antibodies are composed of individual monoclonal antibodies that were isolated from human serum. Table 5 of this publication describes 12 monoclonal antibodies that are said to bind to a "conserved region" at amino acids 164-176 of the RSV G protein of subtype A. Five of these were tested for affinity to the G protein and affinities in the range of 100-500 pM were found. Two of these antibodies were tested for neutralizing ability using the plaque reduction neutralization test (PRNT); one showed an $EC_{50}$ value of approximately 2.5 µg/ml and the other failed to display neutralization characteristics at all.

DISCLOSURE OF THE INVENTION

Antibodies that are specifically immunoreactive with the RSV G protein as compared to the F protein, including those that are immunoreactive with strains of both groups A and B, that have high affinity for the G protein and potent neutralizing ability, have been identified from human donors confirmed as having been recently infected by RSV. In addition, a murine anti-G protein antibody, originally disclosed by Anderson, et al., *J. Virol.* (1988) 62:4232-4238, has been modified so as to minimize the chance of immunological rejection when administered to human subjects. The antibodies of the invention are useful as therapeutic agents and also to increase resistance to RSV in human subjects. Specifically, antibodies to the conserved motif within positions 160-176 of the G protein of subtype A are therapeutically effective in clearing the virus from subjects that are already infected and in reducing the airway inflammation characteristic of RSV infections, as well as for prophylactic use.

Thus, in one aspect, the invention is directed to monoclonal antibodies or immunoreactive fragments thereof that bind an epitope within approximately positions 160-176 on the G protein of the A strain of RSV and that are minimally immunogenic when administered to a human subject. These antibodies display neutralizing capabilities in standard plaque forming assays for neutralization of RSV and demonstrate $EC_{50}$ in such assays of <500 ng/ml, preferably <200 ng/ml, more preferably <100 ng/ml. The antibodies of the invention also have affinities for the G protein of RSV-A2 of <1 nM, preferably <500 pM, more preferably <100 pM. The antibodies of the invention, in one embodiment, bind within 30 residues of, or directly to, at least a portion of the CX3C chemokine motif contained in the G protein of RSV, in a region that has a high degree of amino acid identity across multiple strains of RSV. The CX3C chemokine motif is at approximately amino acid positions 182-186 of strain RSV-A2 and at the corresponding positions of the G protein in other strains. It has been found that the relevant region, within which the antibodies of the invention bind, is included within residues 160-176 of the G protein of RSV-A2 and the corresponding positions of the G protein in other strains. This region is highly conserved within the A strain and contains only a few amino acid differences between the A and B strains. A particularly highly conserved region has the sequence HFEVFN-FVPCSIC (SEQ ID NO:1) at positions 164-176 of RSV A2. Preferably, the antibodies of the invention bind an epitope that includes the sequence FEVFNF (SEQ ID NO:2) or the sequence VFNFVPCSIC (SEQ ID NO:3). In one embodiment, the antibodies of the invention are immunoreactive with this region of conserved amino acid identity and, thus, with G protein of both group A and group B strains of this virus, and therefore with the G-protein of most strains.

For use in the methods of the invention to treat RSV infection or to enhance resistance to RSV, the monoclonal antibodies or fragments of the invention may be immunoreactive with a multiplicity of strains in both groups A and B and a single monoclonal antibody may suffice to have the desired effect. Alternatively, the subject to be treated or to be made resistant may be administered more than a single monoclonal antibody, in particular where one antibody in the protocol is more highly reactive with the strains of group A and the other more highly reactive with the strains of group B.

The invention also includes pharmaceutical compositions useful for prophylaxis or treatment including ameliorating inflammation which contain as an active agent a single antibody or immunoreactive fragment of the invention, or no more than two antibodies or fragments of the invention.

Other aspects of the invention include methods of using the antibodies to treat RSV in human subjects or to induce resistance in these subjects.

The monoclonal antibodies of the invention may be produced recombinantly and therefore the invention also includes recombinant materials for such production as well as cell lines or immortalized cells and non-human multicellular organisms or cells thereof, or microbial cells, for the production of these antibodies. In one embodiment, cells obtained from human subjects are produced in "immortalized" form wherein they have been modified to permit secretion of the antibodies for a sufficient time period that they may be characterized and the relevant encoding sequence cloned.

BRIEF DESCRIPTION OF THE DRAWINGS

FIG. 3 shows the results of probing an illustrative murine monoclonal antibody (131-2G) against an array of peptides with overlapping sequences (SEQ ID NOS:8, 17-23). This work identifies the epitope to which the mAb binds. In the instance illustrated, the epitope is within 30 residues of the CX3C motif (SEQ ID NOS:24-27).

FIGS. 4A-4D: Panels A and B present summary plots of blood from two donors. Panel A shows a donor that has a useful frequency of Ga/Gb cross-reactive clones. Panel B shows a donor that does not. Each point in the plot delineates the relative binding to three probes for a single clone's secreted antibody footprint. Panel C is the quantitative profile of the secreted protein footprint of a single EBV transformed B cell. Panel D shows the profiles of 4 progeny cells from a HEK293 cell transformed with antibody genes from the cell in panel C. This profile is identical to that in panel C, within the precision of the assay as defined by replicates in panel D.

FIGS. 5A-5B show the sequences of heavy chains (panel A) (SEQ ID NOS:28-41)and light chains (panel B) (SEQ ID NOS:42-55) for representative antibodies of the invention.

MODES OF CARRYING OUT THE INVENTION

As used herein, the term "treat" refers to reducing the viral burden in a subject that is already infected with RSV or to ameliorating the symptoms of the disease in such a subject. Such symptoms include bronchiolitis, airway inflammation, congestion in the lungs, and difficulty breathing.

The term "confers resistance to" refers to a prophylactic effect wherein viral infection by RSV upon challenge is at least reduced in severity.

"Immortalized cells" refers to cells that can survive significantly more passages than unmodified primary isolated cells. As used in the context of the present invention, "immortalized" does not necessarily mean that the cells continue to secrete antibodies over very long periods of time, only that they can survive longer than primary cell cultures. The time over which secretion of antibody occurs need only be sufficient for its identification and recovery of the encoding nucleotide sequence.

The phrase "minimally immunogenic when administered to human subjects" means that the response to administration in humans is similar to that obtained when human or humanized antibodies are administered to such humans. It is known that human or humanized antibodies do elicit a response in 5-10% of humans treated. This is true even of antibodies that are isolated from humans since there is a certain level of background "noise" in an immune response elicited. The immune response may be humoral or cellular or both. In particular, elevated levels of cytokines may be found in this percentage of individuals.

Figure 2A:
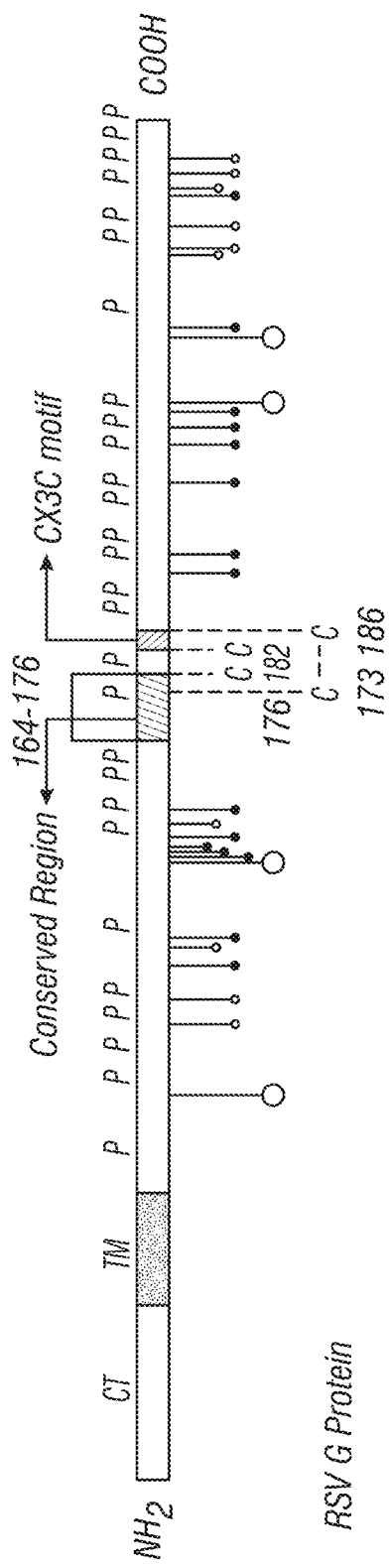
FIG. 2A is a diagram of the RSV G protein indicating the CX3C region and the location of conserved disulfide bonds. The diagrammatic version is generic to all strains, although the specific numbering of positions is slightly different from one strain to the next.

The phrase "conserved region of the RSV G protein" refers to an amino acid sequence contained within 50 amino acids, preferably 30 amino acids, more preferably 20 amino acids on either side of the CX3C region, which is illustrated for a particular strain in FIG. 2A. The conserved region extends mostly at the upstream portion of the G protein from the CX3C-specific region. Thus, using RSV G protein of strain A2 as a model, the conserved region applicable to the antibodies of the invention extends from approximately residue 160 through 188, preferably 160-176.

The antibodies of the invention have a number of desirable properties. First, they are immunoreactive with G protein from a multiplicity of RSV strains, and are typically immunoreactive with G proteins both from A type strains and B type strains. Second, they have quite high affinities for the G protein, some of them in the range of <2 pM. Thus, the antibodies of the invention have affinities of at least 10 nM, preferably 1 nM, more preferably 500 pM, more preferably 100 pM or 50 pM, 10 pM or 1 pM and all values between these preferred exemplary points. Synagis®, a commercial antibody directed to the F protein, is established to have an affinity of about 5 nM. A higher affinity antibody against F protein, Numax™ (motavizumab) is estimated to have an affinity of about 50 pM. The antibodies of the invention show superior ability to behave as therapeutics, and exhibit the capacity to lower the viral count in lungs at the peak of infection. They also exhibit this ability at a point where typically the infection has run its course. This is particularly useful as subjects recovering from RSV infection may continue to shed virus, and thus be able to infect others in a post-clinical setting. The antibodies and fragments thereof also treat the symptoms of infection, including inflammation in the lungs.

The antibodies of the invention have been obtained in two exemplary ways. In one approach, an existing monoclonal antibody referenced above, 131-2G, that is known to be immunoreactive with the conserved region of the G protein, was first sequenced and then humanized by fusing a human constant region with modified human variable regions (both heavy and light chains). The variable regions were chosen based on high homology to the variable regions from the 131-2G antibody, then modified to incorporate the hypervariable amino acids from 131-2G. The methods for such humanization are generally known provided the correct selection of amino acid replacements can be determined. In the case of 131-2G, the original hybridoma line expressed more than one light chain, requiring determination of which one was in fact responsible for binding to the RSV conserved motif. This has been determined by the present inventors and, in one embodiment, the antibodies of the invention are exemplified by the humanized form of mAb 131-2G.

In an alternative method, the antibodies of the invention have been recovered from RSV exposed human donors using the proprietary CellSpot™ method which is described in U.S. Pat. No. 7,413,868, PCT publications WO 2005/045396 and WO 2008/008858, all incorporated by reference.

Figure 1:
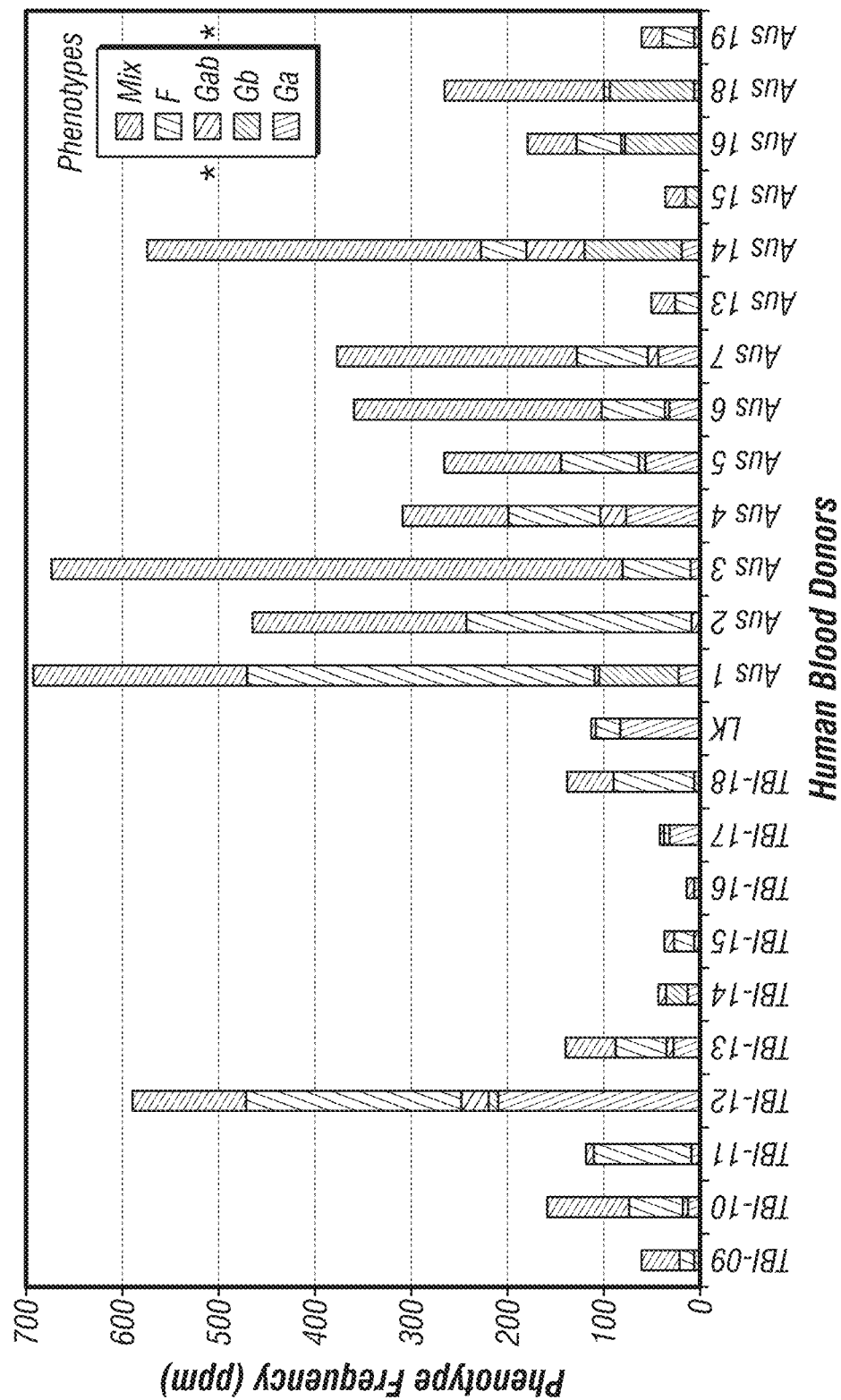
FIG. 1 is a plot showing the frequency in ppm of antibodies to various RSV antigens from human subjects. The desired strain-independent anti-G phenotype (Gab) is quite rare, around 10 parts per million (ppm) overall and as low as 1 ppm in certain subjects. "Mix" refers to antibodies binding both F and G; as F and G have no sequence homology, the binding is likely attributable to shared carbohydrate determinants.

In this method, 40 RSV-infected donor samples were analyzed, in a process yielding ~500,000 antibody-producing cells per blood sample. Thus, in total, there were ~20,000,000 different B cells analyzed for production of antibodies which are specific to the conserved region of the G protein. Only ~10% of the donors had a useful frequency of Ga/Gb specific clones (i.e., strain independent), and such clones were only present at ~1/50,000 cells even in the highest frequency specimens. Overall, the frequency of the desired cells was ~0.003%, which is low enough to be impractical to recover by standard methods but readily accessible using CellSpot™. FIG. 1 shows the spectrum of reactivities to RSV antigens for 24 donors. As shown in this figure, even in those individuals where antibodies crossreacting with both A and B strain-derived G protein were found, the prevalence of these antibodies is much smaller than that of antibodies immunoreactive with F protein or with Ga or Gb alone. A surprisingly large number of clones recognized both the F and G protein (denoted "mix"), which are likely recognizing shared carbohydrate determinants. Affinities of such anti-carbohydrate antibodies are typically poor and were excluded from further consideration. The highest affinity antibody found within this cohort of donors, with an affinity of 1 pM, came from one of the donors with a very low frequency of Ga/Gb specific clones, ~1 ppm. That is, finding this highly favorable clone would have been unlikely without comprehensive screening of the full repertoire from all donors.

In order to perform this screen, B cells were immortalized with Epstein-Barr Virus and assessed according to the above-described methods (see Example 2 for details). Successful B cells were identified and the nucleotide sequences encoding the identified monoclonal antibodies were obtained and sequenced. These were then manipulated recombinantly to produce antibodies in a mammalian cell line.

An important aspect of the G protein function resides in a secreted form of the protein, s(G), created by an alternative splice site near residue 50. Engineering virus to lack s(G) resulted in reduced level of pulmonary infiltrating cells (Maher, et al., *Microbes Infect.* (2004) 6:1049-1055). Conversely, priming mice with s(G) augments IL-5 production and lung eosinophilia (Johnson, et al., *J Virol* (1998) 72:2871-2880). Accordingly, suppressing the activity of s(G) is important for effective treatment of RSV. Achieving that goal requires a high affinity antibody, as is generally known in the art (e.g., U.S. Pat. No. 7,083,950). Since the central conserved region is specifically implicated in the function of s(G) as an immuno-modulatory agent, an effective antibody against s(G) should target this motif.

Figure 2B:
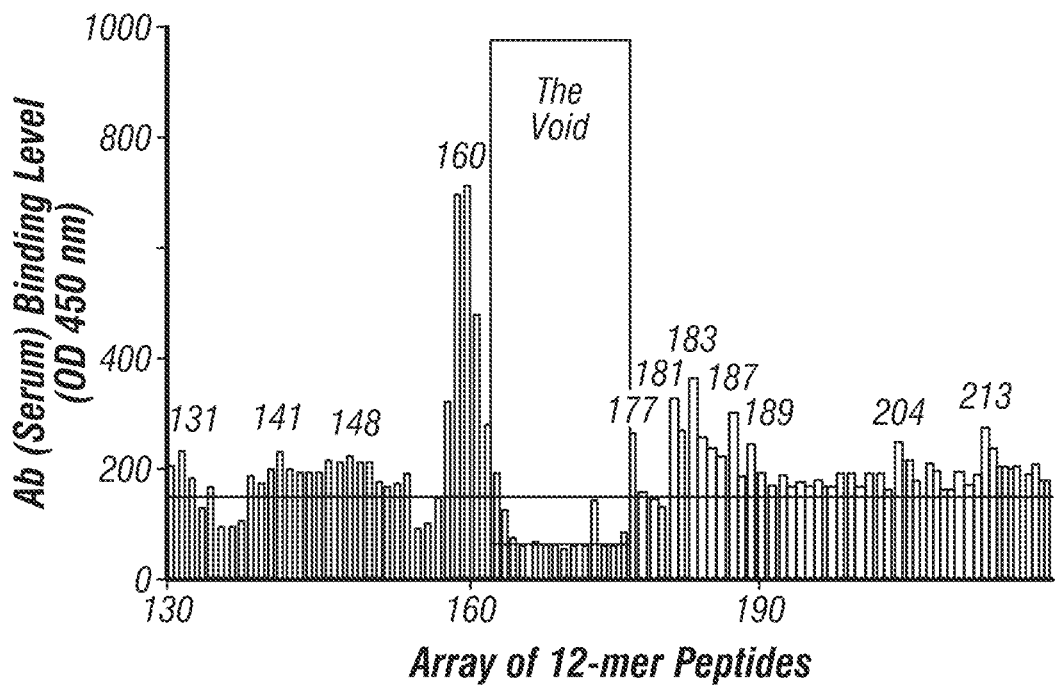
FIG. 2B plots serum binding from RSV exposed subjects against a panel of overlapping 12-mer peptides from RSV G protein, revealing poor immunogenicity of the central conserved region.
Figure 2C:
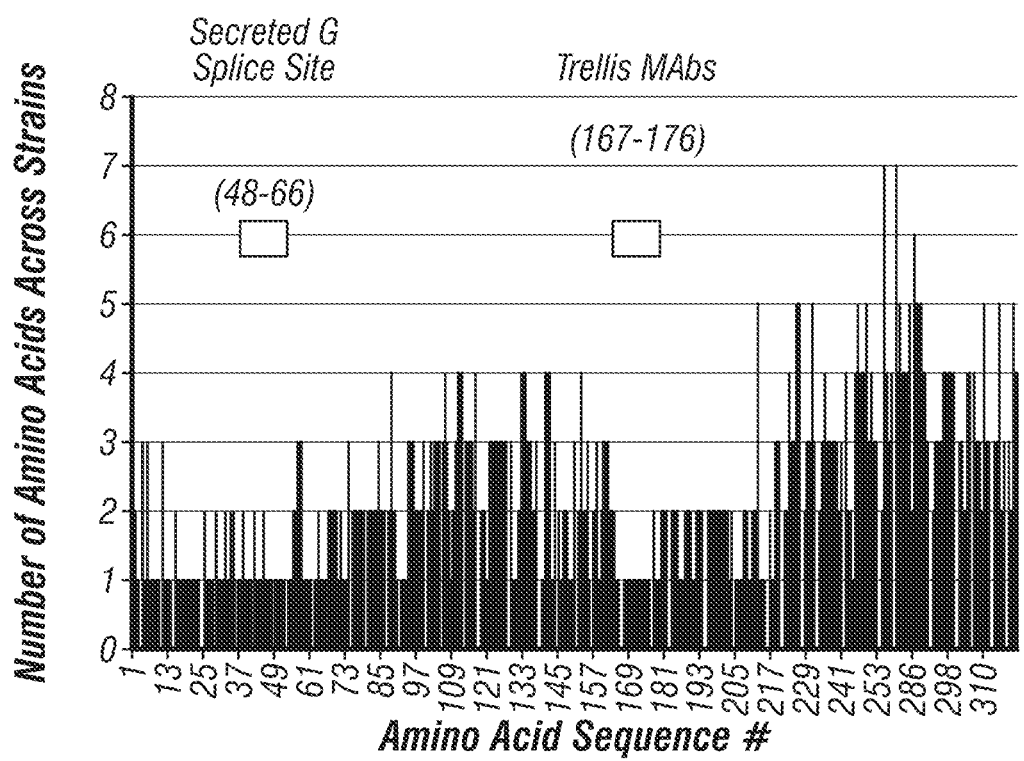
FIG. 2C plots polymorphism frequency for a collection of over 75 RSV strains as a function of position in the G protein, revealing striking conservation at the central conserved region and at the alternative splice site that creates a soluble form of the G protein.

Our survey of the human B cell repertoire from RSV exposed subjects was unbiased in its search for antibodies that bind to the G protein from both strains A and B (Ga/Gb cross-reactive antibodies). Because the survey was comprehensive (40 subjects, ~500,000 B cells examined from each), it is a striking finding that all of the Ga/Gb cross-reactive antibodies binding linear epitopes suitable for mapping recognize epitopes within a few residues of each other, within the central conserved region. This region is known to be poorly immunogenic, as summarized in FIG. 2B (Plotnicky-Gilquin, et al., *Virology* (2002) 303:130-137), consistent with the low frequency of high affinity clones to this region reported here. We have further characterized this region by examining the published sequences of G proteins from >75 RSV isolates. Most residues of the protein show several to many polymorphisms in the collection. Two regions are strikingly free of polymorphisms: the alternative splice site that creates s(G) and the central conserved region to which all Ga/Gb cross-reactive antibodies bind (FIG. 2C). That is, we have discovered that a region which is highly conserved, indicating critical functionality, is also poorly immunogenic. A variety of mechanisms may account for that poor immunogenicity, for example absence of nearby proteolytic cleavage sites suitable for effectively presenting the region in combination with histocompatibility antigens for display to the rest of the immune system. Whatever the mechanism, this surprising result is clear: those viruses that have survived show low immunogenicity to this region. We therefore predicted that augmenting the immune system's activity against this region, by passive transfer of suitable antibodies, would be efficacious, and this has proven to be the case in our animal models. The alternative splice site, although equally conserved, is not unusually low in immunogenicity suggesting that its importance is only with regard to creation of s(G), thus making it a poor target for passive immunotherapy.

Production of the human or humanized antibody of the invention is accomplished by conventional recombinant techniques, such as production in Chinese hamster ovary cells or other eukaryotic cell lines, such as insect cells. Alternatively, techniques are also known for producing recombinant materials, including antibodies, in plants and in transgenic animals, for example in the milk of bovines, or in microbial or plant or insect derived single cell systems.

In addition, since the nucleotide sequences encoding the antibodies are available, the relevant fragments which bind the same epitope, e.g., Fab, F(ab')$_2$ or F$_v$ fragments, may be produced recombinantly (or by proteolytic treatment of the protein itself) and the antibody may be produced in single-chain form. A variety of techniques for manipulation of recombinant antibody production is known in the art.

For use in therapy, the recombinantly produced antibodies or fragments are formulated into pharmaceutical compositions using suitable excipients and administered according to standard protocols. The pharmaceutical compositions may have as their sole active ingredient a monoclonal antibody or fragment of the invention, especially a monoclonal antibody or fragment that is crossreactive with G protein of both A and B strains. Alternatively, two monoclonal antibodies may be the sole active ingredients wherein one more strongly reacts with the A strain G protein and the other more strongly with the B strain G protein. In all of these cases, additional therapeutic agents may be present, including one or more antibodies that is immunoreactive with the F protein or other therapeutic agents that are effective against RSV or inflammation. Thus, anti-inflammatories such as both steroidal and non-steroidal anti-inflammatory compounds may be included in the compositions. Also, the compounds may include nutritional substances such as vitamins, or any other beneficial compound other than an antibody.

In one embodiment, when the formulations for administration are used in order to increase resistance to infection, complete antibodies, including the complement-containing Fc region are employed. Typically, the antibodies are administered as dosage levels of 0.01-20 mg/kg of human subjects or in amounts in the range of 0.01-5 mg/kg or intermediate amounts within these ranges. In one embodiment, amounts in the range of 0.1-1.0 mg/kg are employed. Repeated administration separated by several days or several weeks or several months may be beneficial. Boosters may also be offered after one or two or five or ten years.

In another embodiment, for a therapeutic effect in order to reduce viral load, complete antibodies, containing the complement-containing Fc region are also employed. The amounts administered in such protocols are of the order of 0.001-50 mg/kg or intermediate values in this range such as 0.01, 1 or 10 mg/kg are employed. Repeated administration may also be used. The therapeutic treatment is administered as soon as possible after diagnosis of infection, although administration within a few days is also within the scope of the invention. Repeated administration may also be employed. In order to reduce the inflammatory response in the lungs, only the immunospecific fragments of the antibodies need be employed. Dosage levels are similar to those for whole antibodies. Administration of mixtures of immunospecific fragments and entire antibodies is also included within the scope of the invention.

Administration of the antibody compositions of the invention is typically by injection, generally intravenous injection. Thus, parenteral administration is preferred. However, any workable mode of administration is included.

The formulations are prepared in ways generally known in the art for administering antibody compositions. Suitable formulations may be found in standard formularies, such as *Remington's Pharmaceutical Sciences*, latest edition, Mack Publishing Co., Easton, Pa., incorporated herein by reference. The formulations are typically those suitable for parenteral administration including isotonic solutions, which include buffers, antioxidants and the like, as well as emulsions that include delivery vehicles such as liposomes, micelles and nanoparticles.

The desired protocols and formulations are dependent on the judgment of the attending practitioner as well as the specific condition of the subject. Dosage levels will depend on the age, general health and severity of infection, if appropriate, of the subject.

The following examples are offered to illustrate but not to limit the invention.

EXAMPLE 1

Cloning and Humanization of 131-2G

Cloning and sequencing of mAb 131-2G. Total mRNA was extracted from 131-2G hybridoma according to the manufacturer's directions (RNeasy™ kit: Qiagen Santa Clarita, Calif.). Seven family-specific 5' VγER1 primers designed to target the VH1 through VH7 gene families of Igγ, and one consensus 3' Cγ1 primer were used to amplify and sequence the variable region of 131-2G heavy chain. One consensus 5' Vk primer was designed to amplify each of the Vk families, and one reverse primer specific to the kappa constant region were used to amplify and sequence the kappa light chain. The VH and VL transcripts were amplified from 100 ng total RNA using reverse transcriptase polymerase chain reaction (RT-PCR).

Two PCR reactions were run for the 131-2G hybridoma: one for light chain kappa (κ) and one for gamma heavy chain (γ1). The QIAGEN® OneStep RT-PCR kit was used for amplification, (Qiagen Catalog No. 210212). The extracted PCR products were directly sequenced using specific constant region primers. The derived sequences were compared to known germline DNA sequences of the Ig V- and J-regions using the V-BASE2 and by alignment of VH and VL genes to the mouse germ line database. Sequence analysis: from the nucleotide sequence information, data regarding V and J gene segment of the heavy and light chain of 131-2G were obtained. Based on the sequence data new primer sets specific to the leader sequence of the Ig VH and VK chain of 131-2G were designed. V gene usage and sequence analysis: Heavy chain genes of 13-12G were from the VH1 germline gene family, the germline gene for the D region is DSP2.2 and the J region was from the JH3 germline. Light chain genes were from Vkappa 1(K1A5) and Jkappa4, germline gene families.

```
131-2G uses a V segment of the IgH-VJ558 VH1 family
(SEQ ID NOS: 4-5):
      M   G   W   S   W   I   F   L   F   L   L   S   G   T   A   G   V   H   S   E
    1 ATGGGATGGA GCTGGATCTT TCTCTTCCTC CTGTCAGGAA CTGCAGGTGT CCACTCTGAG V   Q   L   Q   Q   S   G   P   E   L   V   K   P   G   T   S   V   K   I   S
   61 GTCCAGCTGC AACAGTCTGG ACCTGAACTG GTGAAGCCTG GAACTTCAGT GAAGATATCC C   K   A   S   G   Y   S   F   T   G   F   T   M   N   W   V   K   Q   S   H
  121 TGCAAGGCTT CTGGTTATTC ATTCACTGGC TTCACCATGA ACTGGGTGAA GCAGAGCCAT G   K   N   L   E   W   F   G   L   I   N   P   F   N   G   N   T   G   Y   N
  181 GGAAAGAACC TTGAGTGGTT TGGACTTATT AATCCTTTCA ATGGTAATAC TGGCTACAAC
```

-continued

```
        Q   K   F   K   G   K   A   T   L   T   V   D   K   S   S   S   T   A   F   M
241 CAGAAGTTCA AGGGCAAGGC CACATTAACT GTAGACAAGT CTTCCAGCAC AGCCTTCATG

E   L   L   S   L   T   S   E   D   S   A   V   Y   Y   C   A   R   S   G   K
301 GAGCTCCTCA GTCTGACATC TGAGGACTCT GCAGTCTATT ACTGTGCAAG ATCGGGAAAA

S   Y   D   Y   E   A   W   F   T   Y   W   G   Q   G   T   L   V   T   V   S
361 TCCTATGATT ACGAGGCCTG GTTTACTTAC TGGGGCCAAG GGACTCTGGT CACTGTCTCT

A
421 GCA 131-2G uses a V segment of the IgKV1 subgroup
(SEQ ID NOS: 6-7):
        D   I   V   M   T   Q   T   T   L   S   L   P   V   S   L   G   N   Q   A   S
  1 GATATTGTGA TGACACAAAC TACACTCTCC CTGCCTGTCA GTCTTGGAAA TCAAGCCTCC I   S   C   R   S   S   Q   T   I   V   H   T   N   G   N   T   Y   L   E   W
 61 ATCTCTTGCA GATCTAGTCA GACCATTGTA CATACTAATG GAAACACCTA TTTAGAATGG Y   L   Q   K   P   G   Q   S   P   K   L   L   I   Y   K   V   S   N   R   F
121 TACCTGCAGA AACCAGGCCA GTCTCCAAAG CTCCTGATTT ACAAAGTTTC CAACCGATTT S   G   V   P   D   R   F   S   G   S   G   S   G   T   D   F   I   L   N   I
181 TCTGGGGTCC CAGACAGGTT CAGTGGCAGT GGATCAGGGA CAGATTTCAT ACTCAATATC S   R   V   E   A   E   D   L   G   V   Y   Y   C   F   Q   G   S   H   V   P
241 AGCAGAGTGG AGGCTGAGGA TCTGGGAGTT TATTACTGCT TTCAAGGTTC ACATGTTCCA F   T   F   G   S   G   T   K   L   E   I   K   R
301 TTCACGTTCG GCTCGGGGAC AAAGTTGGAA ATAAAACGGA
```

Humanization of mAb 131-2G. The binding of an Antibody (Ab) to its cognate Antigen (Ag) is a highly specific interaction. This specificity resides in the structural complementarity between the Ab-combining site and the antigenic determinant. Ab-combining sites are made up of residues that are primarily from the hypervariable or complementarity determining regions (CDRs); occasionally, residues from non-hypervariable (or framework) regions influence the overall domain structure and, hence, the combining site.

The mouse VH gene segment repertoire is twice the size of that in humans and contains more functional genes, compared with the human IgH locus. The mouse and the human loci bear no large-scale similarity to each other. The first two CDRs of VH and VL domains have a small repertoire structure of main chain conformation known as the canonical structures. The existence of a particular canonical structure is mainly determined by the length of the CDRs and the presence of key residues at particular sites in the sequence. The same canonical structure combinations of VH1 family (VH1 1-2) are shared between the members of human VH1 and mouse VH1 families. Based on the sequence analysis of heavy and light chains of 131-2G and the fact that 131-2G uses V segments of IgH-VJ558 VH1 family and Igκ1 family, both chains were aligned and compared to the members of the human VH1 and VK1 families. Sequence homology was found to be 70% and 77% identity to the germ line sequence of Human VH1-8 and Vk1-18 respectively. These germ lines were picked as the human framework for the humanized 131-2G mAb.

Epitope mapping of mAb 1312G. Western Blot analysis using RSV lysate and purified Ga protein suggested that 131-2G recognizes a linear epitope. The binding domain of 131-2G was mapped using a set of overlapping peptides derived from the RSV-GA2 protein sequence. FIG. 2A diagrams the G protein sequence, including location of the conserved CX3C motif. In order to obtain a fine epitope mapping, a scan was performed on a family of 12-mer Ga derived peptides, each shifted by one residue. An array of such peptides was probed with 131-2G mAb, at 1 μg/ml. Binding of 131-2G was detected by goat anti mouse peroxidase-labeled antibody in combination with the super signal chemiluminescence detection system (Pierce, Rockford Ill., USA). As summarized in FIG. 3, the 131-2G antibody reacts with 8 consecutive peptides spanning the RSV-Ga protein from residue 157 to 176. The epitope recognized by 131-2G is within the peptide sequences (157) SKPNNDFHFEVF (169) (SEQ ID NO:8) and (169) HFEVFNFVPCSI (176) (SEQ ID NO:9). Based on the common sequence from the 8 peptides, the 131-2G binding domain was mapped to residues 164-168.

Three methods were used to characterize the affinity of 131-2G and analogous human mAbs. First, binding signal was measured for a fixed amount of antibody probed against serial dilutions of antigen in an ELISA format. The midpoint of this titration curve is an approximation of the affinity. In the case of 131-2G, that midpoint is 4 nM. Second, the affinity of 131-2G was measured by Biacore analysis at a commercial analytical laboratory; based on the ratio of on-rate to off-rate, the affinity was calculated as 7 nM. Third, dilution of the Ga protein on CellSpot™ beads with serum albumin reduces the opportunity for multiple copies of the protein to interact with the antibody footprint. The resulting suppression of multidentate avidity effects from the raw signal allows rank ordering of a set of clones for affinity, relative to a known standard. This measure of affinity can be used to compare the human antibodies to 131-2G and efficiently select for high affinity clones. All of these methods are improved by availability of a consistent source of G protein antigen. In our early studies, antigen was extracted from virus infected cells. Due to variability in the quality of antigen prepared this way, we developed a recombinant expression system for producing the G protein, which proved to be more reliable.

EXAMPLE 2

Isolation of Human B Cells Secreting Antibody to RSV-Ga/Gb

Peripheral blood mononuclear cells from 40 adults with confirmed RSV infection were surveyed for human B cells producing anti-viral antibodies. Subjects with the desired antibodies against RSV attachment G protein were used for cloning of anti RSV-G specific mAbs. The result of the survey was that ~10% of the subjects had a frequency of the desired cells greater than 1 in 100,000. Even those with a lower frequency, however, were of interest and in fact the highest affinity antibody identified came from a donor with a very low frequency of the desired B cell type, ~1 ppm.

To accomplish the survey and recovery of rare favorable cells, we used the previously described CellSpot™ technology. The CellSpot™ assay method effectively shrinks an ELISA equivalent assay down to a virtual well of near single cell dimensions by capturing secreted IgG from a single cell as a footprint in the vicinity of the cell. As a result, millions of cells can be readily analyzed. Further, by use of microscopic multiplexing reagents (combinatorially colored fluorescent latex microspheres, cf U.S. Pat. No. 6,642,062), each clone's secreted antibody footprint can be characterized in detail for specificity and/or affinity using multiple biochemical probes. The fidelity of the quantitative assay is sufficient to enable rescue of extremely rare favorable cells from the survey population, with the cloned expression cell showing a phenotype consistent with the original identifying assay.

The screening criteria were: binding to G protein from both of the two major strain families, denoted Ga and Gb, and not binding to the F protein (the other major viral coat protein). Affinity rank ordering of clones can also be accomplished by diluting the antigen on the bead with serum albumin This reduces the chances for multi-dentate binding to the secreted IgG footprint (an "avidity" effect), thus selecting for higher intrinsic affinity. G protein was purified from Vero cells infected with one or the other of the two RSV strains.

Applied to human B cells, the method begins by depleting non-B cells from PBMCs using standard magnetic separation methods. Cells were resuspended in IMDM/20% HI-FCS at 1e6/ml; EBV (direct pelleted from the supernatant of infected B95-8 cells) was added at 1:100 dilution, and the cells incubated 2 hr at 37° C. Excess virus was washed away, and cells either: cultured at 2e6/ml in IMDM, 20% HI-FCS, 20% Giant cell tumor conditioned medium, 2 µg/ml CpG (ODN2006), and 10 ng/ml IL-10 for surveying only, or further selected for surface IgG using magnetic positive selection. Cells were cultured at 200-300 cells/well on irradiated human lung cells (MRC-5, 5,000 cells/well) in IMDM, 20% HI-FCS, 20% Giant cell tumor conditioned medium, 2 µg/ml CpG (ODN2006), and 10 ng/ml IL-10. Medium was supplemented every 2-3 days. One half of the contents of the wells were assayed in CellSpot™ at day 6. The remaining cells in the small number of wells positive by the survey assay were then diluted to 10, 5, 1, and 0.5 cells/well with the same feeder cells and culture conditions. After 4-5 days these limiting dilution plates were again assayed by ELISA or CellSpot™.

Contents of positive wells at limiting dilution were then processed using Reverse Transcriptase-PCR to recover the encoding polynucleotide for the antibody heavy and light chains. Total time from thawing PBMCs to recovery of the encoding mRNA sequence via RT-PCR was 10-12 days.

Figure 4A:
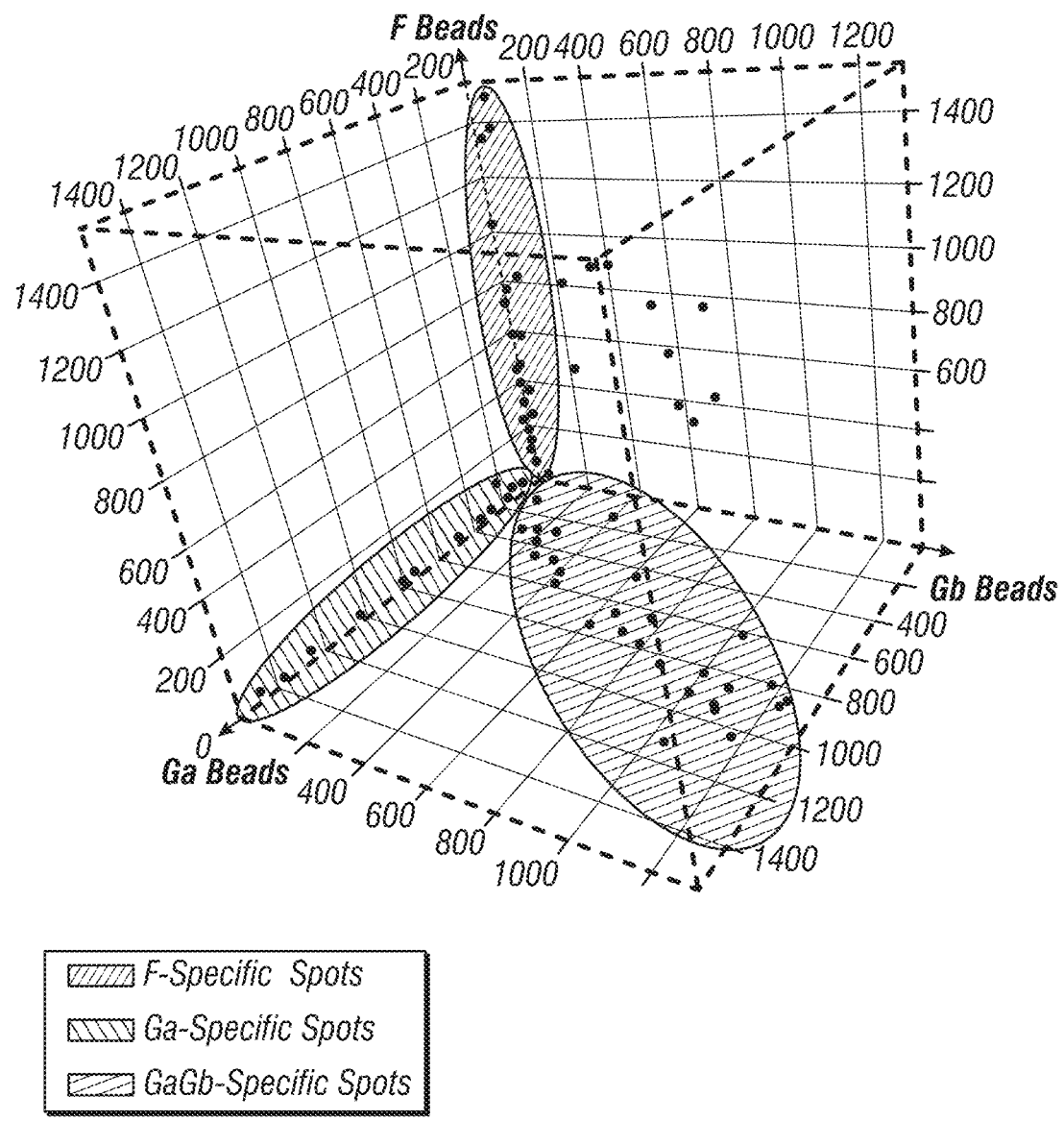
Figure 4B:
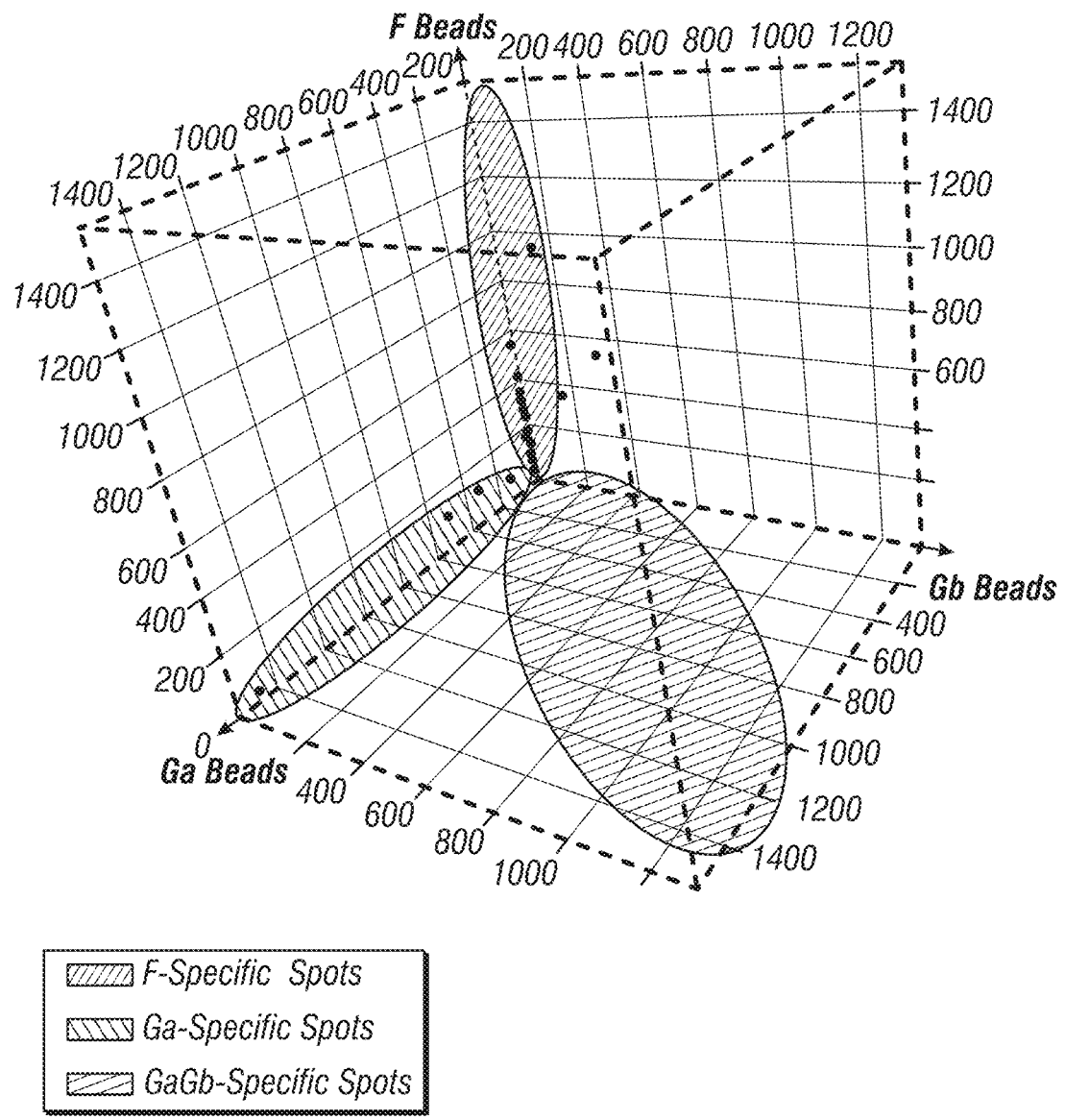
Figure 6A:
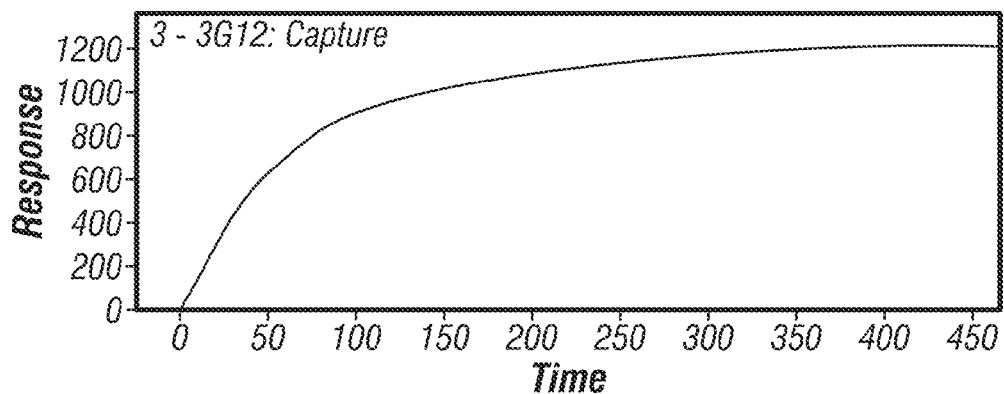
FIGS. 6A-6F show Biacore results on determinations of affinity of two antibodies of the invention. As shown in panels E and F, antibody 3D3 binds the G protein and does not shows a barely detectable off rate. Panels A and D show binding of the antibody to the sensor surface. Panels B and E show the increase in sensor signal as Ga protein flows across the surface and is captured by the bound antibody, followed by a decline in signal as the surface is washed with buffer allowing the bound Ga protein to desorb from the surface. Panels C and F similarly show on-rates and off-rates for the Gb protein.
Figure 6B:
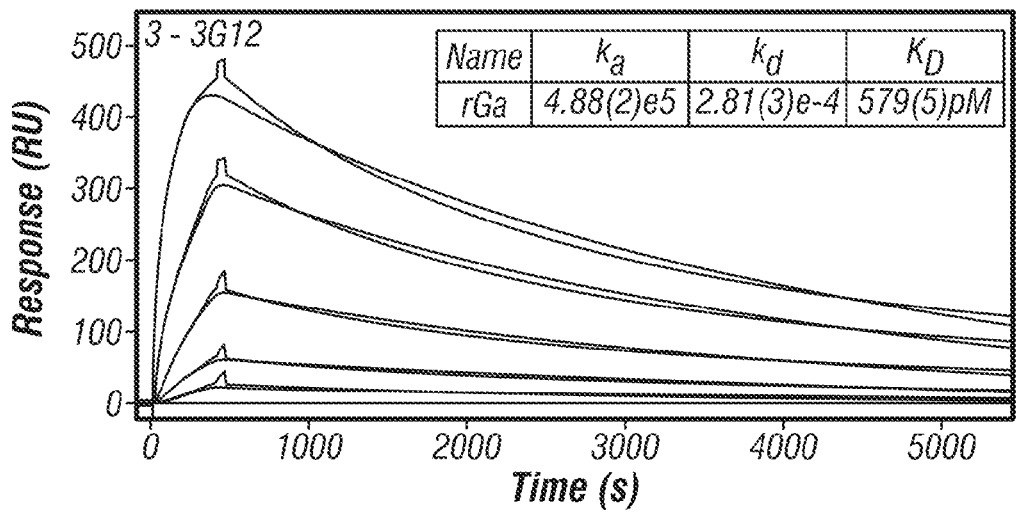
Figure 6C:
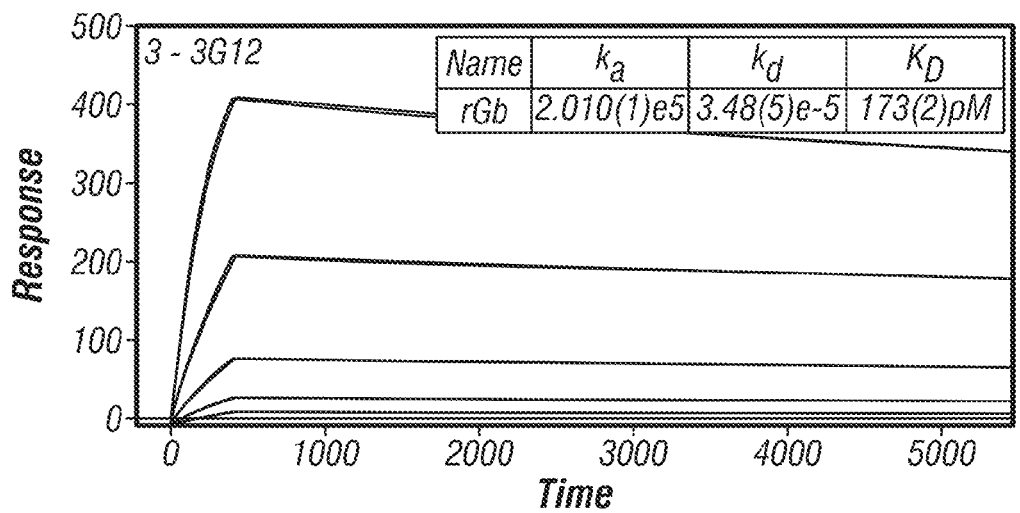
Figure 6D:
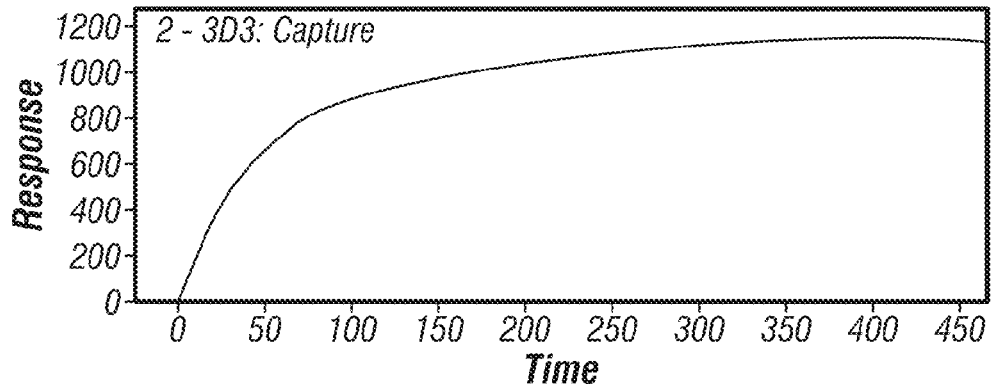
Figure 6E:
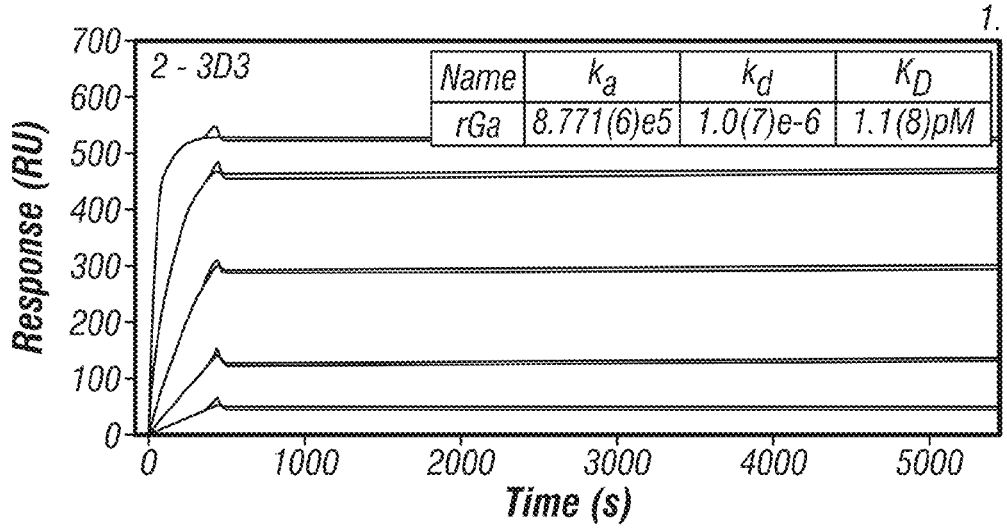
Figure 6F:
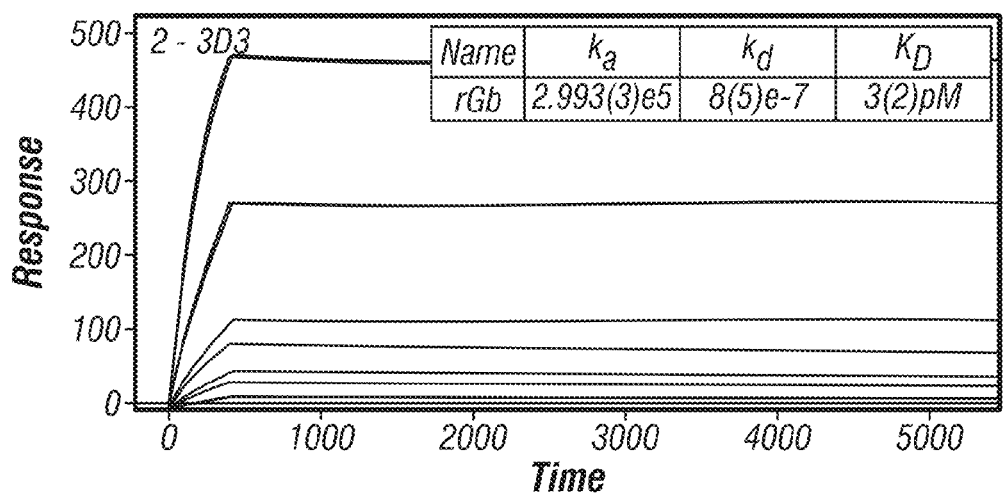
Figure 7:
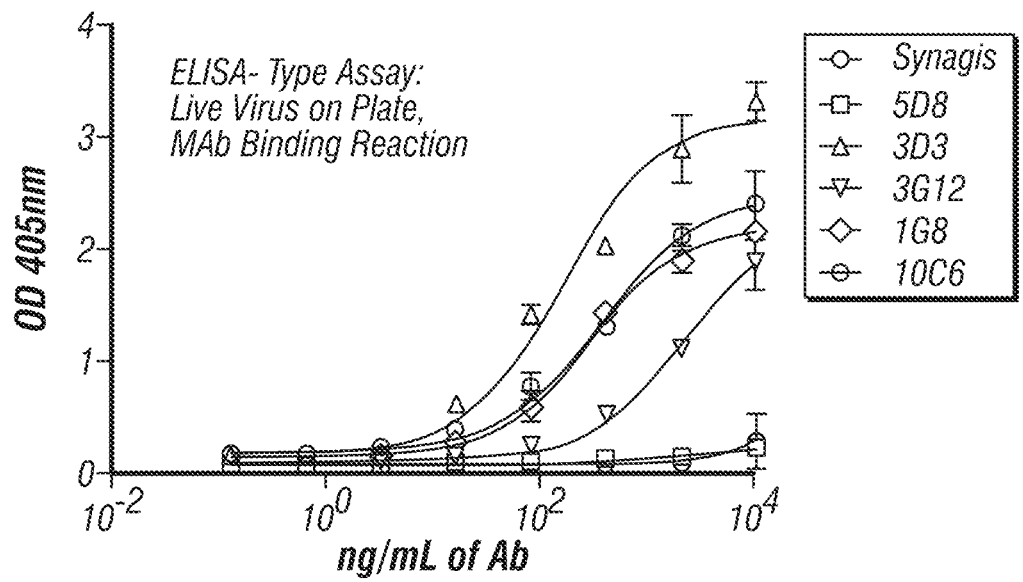
FIG. 7 is a graph of the binding of various antibodies of the invention as compared to the Synagis® F protein-binding antibody as determined in an ELISA assay using live virus to coat the microplate.
Figure 8:
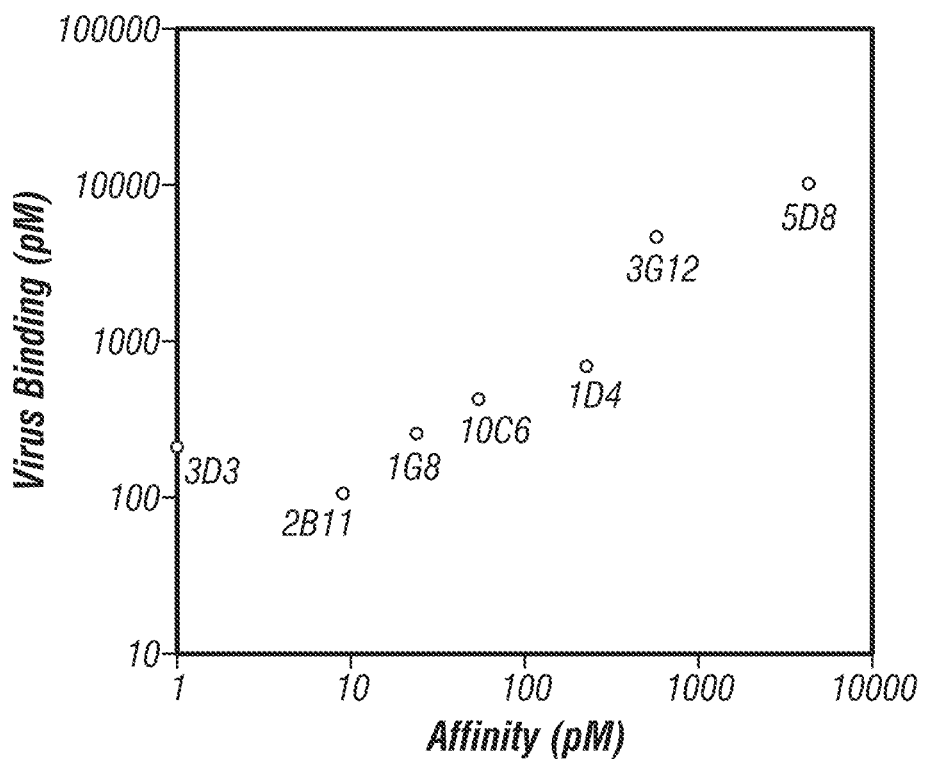
FIG. 8 is a graph plotting affinity to G protein on the X-axis against binding to virus on the Y-axis. The two abilities are correlated, although 3D3 shows slightly less affinity to live virus than would be predicted from its affinity to G protein.
Figure 9A:
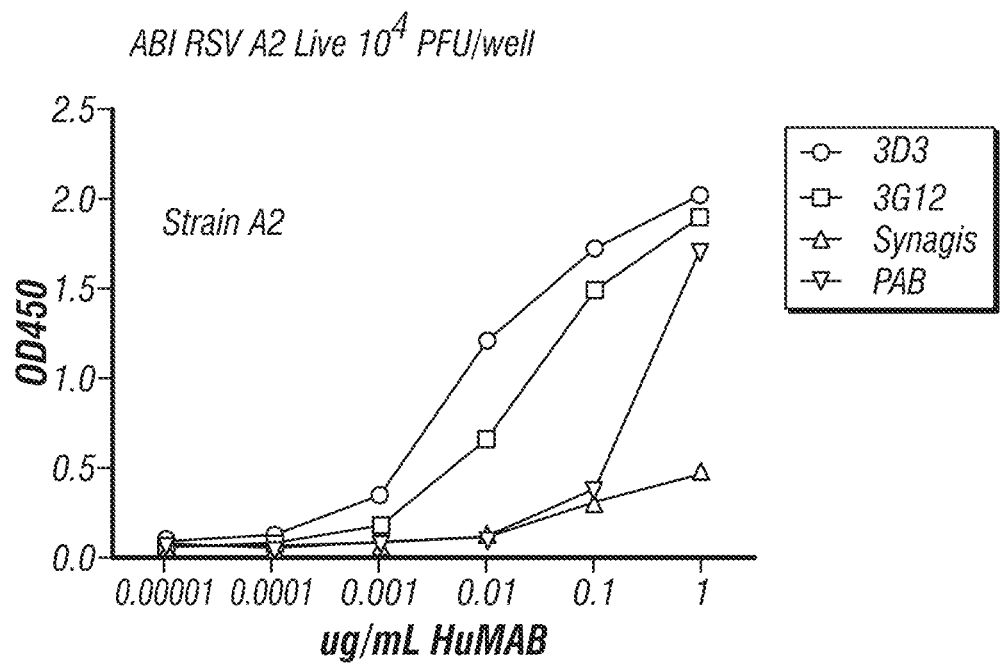
FIGS. 9A and 9B show a comparison of binding of several antibodies to strains A2 and A5.
Figure 9B:
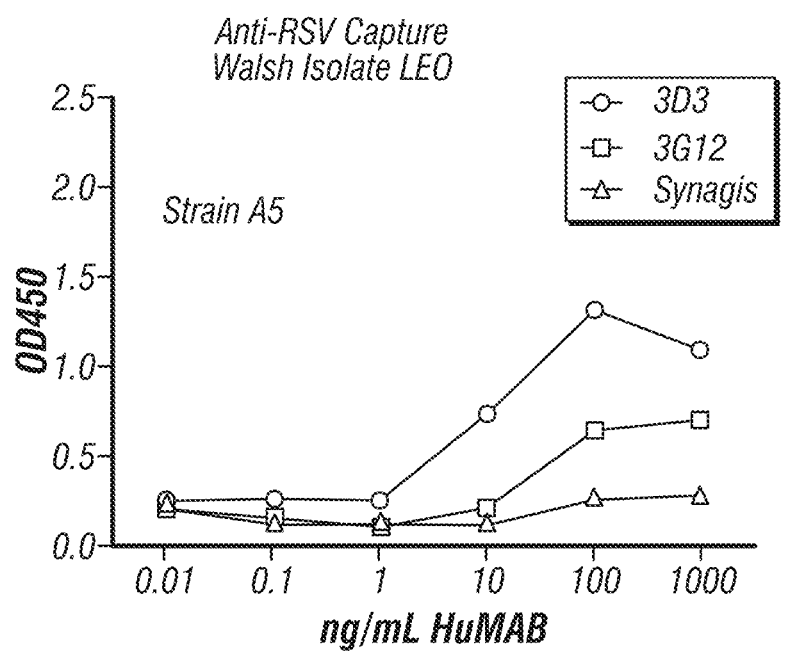

FIG. 4 shows illustrative data from this experiment. Examples of CellSpot™ profiling of favorable and unfavorable donor blood samples is illustrated in panels A and B. The profile of a favorable clone at initial detection is shown in panel C, along with replicate profiles in panel D of antibody secreted from progeny of a HEK293 cell transformed with cDNA cloned antibody derived from that cell. The profiles are identical within the precision of the assay, indicating successful recovery of the favorable clone.

As was shown in FIG. 1, the majority of anti-RSV antibodies are directed to the F protein or to an antigenic determinant shared by F and G (most likely carbohydrate since the two proteins have no sequence homology). Of the G specific antibodies, most bind only Ga or only Gb, consistent with the known high sequence variability of the G protein. Overall, ~20 million individual B cells were surveyed. The 12 most promising antibodies were recovered by RT-PCR. Overall, then, the frequency of favorable clones is below 1 in 1 million, and over 50 million ELISA equivalent assays were needed to find those rare clones. The CellSpot™ technology thus enabled a more comprehensive survey of clones than would otherwise be practical. The quality of the resulting clones is superior to those found by more limiting screening, and the consensus features of that high quality set reveal unanticipated features of the desired antibodies.

EXAMPLE 3

Cloning of Human Antibodies to RSV-Ga/Gb

Amplification of rearranged Ig Heavy and Ig Light genes from positive ELISA wells was accomplished using semi-nested polymerase chain reaction (PCR). For amplification of a priori unknown V-gene rearrangements, a collection of family-specific V-gene primers was constructed, which recognize nearly all V-gene segments in the human Ig Locus. The 5' primers were used together with primer mixes specific for the Cγ, Cκ and Cλ gene segments. The clonality of the limiting dilution RSV-G specific B cells was unequivocally determined by sequence comparison of V-gene amplificates from distinct progeny cells, and the amplified full length V-gene rearrangements were cloned into IgG expression vectors. This method was also useful to address additional issues, such as V-, D-, and J-gene usage and the presence and pattern of somatic mutations.

Methods. Total mRNA from the isolated human B cells was extracted using a commercially available RNA purification kit (RNeasy™; Qiagen (Germany)). Reverse transcription-PCR was done by using total RNA preparations and oligonucleotides as primers. Three PCR reactions were run for each sample: one for light chain kappa (κ) one for light chain lambda (λ), and one for gamma heavy chain (γ). The QIAGEN® OneStep RT-PCR kit was used for amplification, (Qiagen Catalog No. 210212). In the coupled RT-PCR reactions, cDNA is synthesized with unique blend of RT enzymes (Omniscript™ and Sensiscript™) using antisense sequence specific primer corresponded to C-κ, C-λ or to a consensus of the CH1 regions of Cγ genes, RT is preformed at 50° C. for 1 hour followed by PCR amplification of the cDNA by Hot-StarTaq DNA Polymerase for high specificity and sensitivity. Each PCR reaction used a mixture of 5' sense primers. Primer sequences were based on leader sequences of VH, VK and VL. PCR reactions were run at 95° C. for 15 minutes, initial hot start followed by 20 cycles of 95° C. for 30 seconds (denaturation), 60° C. for 45 seconds (annealing) and 72° C. for 1 minute (elongation).

Nested PCR for detection and cloning of the variable Ig fragments into expression vectors. In the second round, an aliquot of 5 µl of the first amplification reaction was applied. The primers used carry the 5'BglII and 3' XbaI restriction sites. Thirty PCR cycles were performed. Identical conditions were used for the first and second rounds of amplification. Five microliters of each reaction were loaded and separated on a 1% agarose gel and then stained with ethidium bromide. The V-C PCR product is predicted to amplify rearranged fragments of VH and VL, 500 and 450 bp respectively. PCR bands with a molecular size of approximately 500 bp indicated a positive result. PCR products were purified (Qiagen gel purification kit catalog number 28704) and the extracted PCR products were directly sequenced using specific constant region primers. The sequences of the cloned fragments were confirmed by sequencing plasmids prepared for recombinant production.

FIG. 5A (SEQ ID NOS:28-41) shows the amino acid sequences of the heavy chains of the antibodies of the invention isolated from human subjects as well as of humanized 131-2G, including variable region, the D and J joining regions, the framework (FR) and complementarity determining (CDR) regions. All of the listed antibodies are immunoreactive with the G protein from both the A and B strains except for antibody 3F9, which is immunoreactive only with G protein from strain A. FIG. 5B (SEQ ID NOS:42-55) shows similar sequence information for the light chains of these antibodies. Dashes in the sequence listings represent alignment corrections in the gene sequences of different lengths.

The PCR fragments described above were digested and cloned into individual expression vectors carrying the constant region of human gamma 1, or of human kappa or lambda, for in vitro antibody production in mammalian cells. The expression vectors coding for heavy and light chains were co-transfected into the 293 (human kidney) cell line (Invitrogen). The expression plasmids were introduced with the use of a cationic lipid-based transfection reagent (293fectin™; Invitrogen). For each transfection reaction, 20 μg of purified plasmids and 40 μL of the 293fectin™ were mixed with 1 mL of Opti-MEM® (Invitrogen) and incubated for 5 min at room temperature before being combined and allowed to form complexes for 20 min at room temperature. The DNA-293fectin complexes were added to 3×10⁶ cells seeded in 90 mm petri plates and incubated at 37° C., 8% CO2. In the final procedure, the supernatant was harvested 72 hrs post-transfection by centrifugation (3,000 g, 15 min at 4° C.), to recover the secreted antibodies.

EXAMPLE 4

Epitope Mapping of the Invention Antibodies and Affinity Determination

Using the technique described in Example 1 with respect to epitope mapping of the prior art antibody 131-2G, the epitopes corresponding to the antibodies of the invention were determined. The affinity of the invention antibodies was determined using the methods described in Example 1 with respect to mAb 131-2G.

As noted in Table 1 below, three of the antibodies bind a conformational epitope—i.e., they do not map by binding overlapping peptides. Antibodies of the invention which map to specific sequences are shown in the table. Also shown are the affinity constants, determined using standard Biacore assays with respect to recombinant Ga and Gb proteins expressed as pM, calculated from the measured on and off rates. The data for two of these antibodies is shown in FIG. 6. Panels A, B and C show binding data for 3G12 and panels D, E and F show the data from 3D3. The top row shows loading of the biosensor chip with antibody, the middle row shows the signal arising from flowing Ga protein across the chip followed by washing with buffer, and the bottom row shows the same thing for Gb protein. The increase in signal allows calculation of the on-rate, while the decrease during washing allows calculation of the off-rate. The ratio of on to off rates is the affinity constant, Kd.

| Bin | reactivity | Epitope | Epitope | SEQ ID NO: | KD × Ga (pM) | KD × Gb (pM) |
|---|---|---|---|---|---|---|
| 1F12 | Ga/Gb | 166-172 | EVFNFVP | 10 | | |
| 3G12 | Ga/Gb | 167-176 | VFNFVPCSIC | 3 | 579 | 173 |
| 1A5 | Ga/Gb | 161-170 | NDFHFEVFNF | 15 | | |
| 3D3 | Ga/Gb | 164-172 | HFEVFNFVP | 56 | 1.1 | 3 |
| 1G1 | Ga/Gb | | conformational | | | |
| 2B11 | Ga/Gb | 162-172 | DFHFEVFNFVP | 12 | 9 | 1.6 |
| 5D8 | Ga/Gb | 160-169 | NNDFHFEVFN | 13 | 4390 | 1 |
| 2D10 | Ga/Gb | | conformational | | | |
| 3F9 | Ga | | Ga only | | | |
| 1D4 | Ga/Gb | 165-171 | FEVFNFV | 14 | 230 | 52 |
| 1G8 | Ga/Gb | 161-170 | NDFHFEVFNF | 15 | 24 | 141 |
| 6A12 | Ga/Gb | | conformational | | | |
| 10C6 | Ga/Gb | 164-168 | *HFEVF | 11 | 55 | 378 |

*same epitope as 131-2G

EXAMPLE 5

Comparison of Binding to G Protein with Binding to Virions

FIG. 7 shows the results of an ELISA assay employing live virus and assessing the binding using a standard horseradish peroxidase assay. Viral preps from various sources were used to coat plates at $10^5$ PFU/well or higher concentration in carbonate buffer at pH 9.6 overnight at 4° C. Plates were blocked in 5% mik with PBST for an hour at room temperature. Serial dilutions of antibodies were added to wells in blocking buffer for one hour at room temperature. For detection, 1:2000 dilution of goat anti-human Fc gamma—HRP (Jackson Immuno.) was added in blocking buffer for one hour at room temperature. Plates were washed extensively in PB ST. Turnover of the substrate TMB was measured at 450 nm. As shown in FIG. 7, 3D3 binds well to the live virus as do a number of other antibodies of the invention. The Synagis® antibody, which has substantially weaker affinity, shows little binding to live virus even at $10^4$ ng/ml antibody. FIG. 8 shows the correlation of the binding to recombinant protein as compared to binding to virus particles.

FIGS. 9A and 9B are graphs that demonstrate comparative ability of the antibodies of the invention to bind to strains A2 versus A5, using the assay described above. FIG. 9A shows that 3D3 and 3G12 bind well to strain A2 as compared to Synagis®. PAB is a commercial polyclonal goat antibody against all RSV proteins (Chemicon, catalog #AB1128).

FIG. 9B shows that these antibodies also bind strain A5; note the units on X-axis are different than in FIG. 9A. Similar experiments show that the antibodies of the invention bind to a wide variety of clinical isolates.

EXAMPLE 6

Neutralization Assays

The ability of selected antibodies of the invention to neutralize virus in vitro was obtained by a standard plaque assay.

HEp2 cells were plated in 12-well plates at 2×10$^5$ cells/well. The following day, serial dilutions of antibodies were generated in media. Approximately 200 PFU/well of RSV was added to the antibodies, in the presence of rabbit complement serum for one hour at room temperature. The antibody-virus mixture was then added to HEp2 cells at 200 uL/well for 2 hr at room temperature to allow for infection. Following this infection period, media were removed and media containing 1% methyl cellulose were added to all wells. Plates were incubated at 35° C. for 6 days, after which time, cells were fixed and stained for plaque number determination, as follows: Methyl cellulose is aspirated from the cell layers, and cells are fixed in 100% methanol for 30 min at room temperature. The plates are then washed 3× with 5% milk in PBS. Primary antibody is added at 1:500 dilution (Goat anti-RSV polyclonal antibody (Chemicon Cat #AB 1128)) in PBS+5% Milk Protein for 1 hr. Plates are washed again 3× with 5% milk in PBS. Secondary antibody is added at 1:500 dilution in 5% milk protein in PBS (ImmunoPure Rabbit anti-goat antibody IgG (H+L) Peroxidase conjugated) (Thermo Scientific, Cat #31402)) for 1 hr. Plates are washed 3× with 1× PBS. Plaques are visualized by adding 1-Step Chloronaphthol substrate Pierce, Cat #34012), 200 µL per well for 10 min Plates are rinsed with water and allowed to air dry. Plaques are counted in each well.

Figure 10:
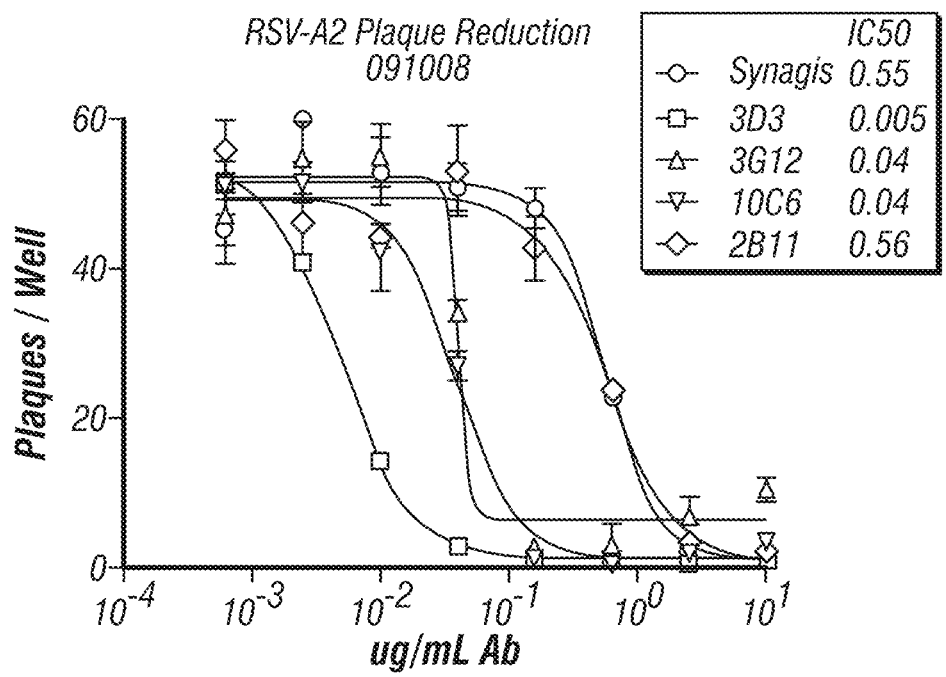
FIG. 10 shows the results of neutralization assays. The results are shown in terms of number of plaques plotted against μg of antibody.

FIG. 10 shows the results in terms of absolute numbers of plaques per µg of human antibody and Synagis® antibody is included in the results. These data show that of the antibodies tested, 3D3 is most potent. 3G12 has an IC$_{50}$ of 15 ng/ml or an affinity of 100 pM according to this assay, whereas Synagis® commercial antibody has an IC$_{50}$ of 300 ng/ml corresponding to an affinity of 2 nM. It was further found that Synagis® and the anti-G antibodies of the invention were not synergistic under these conditions.

Figure 11:
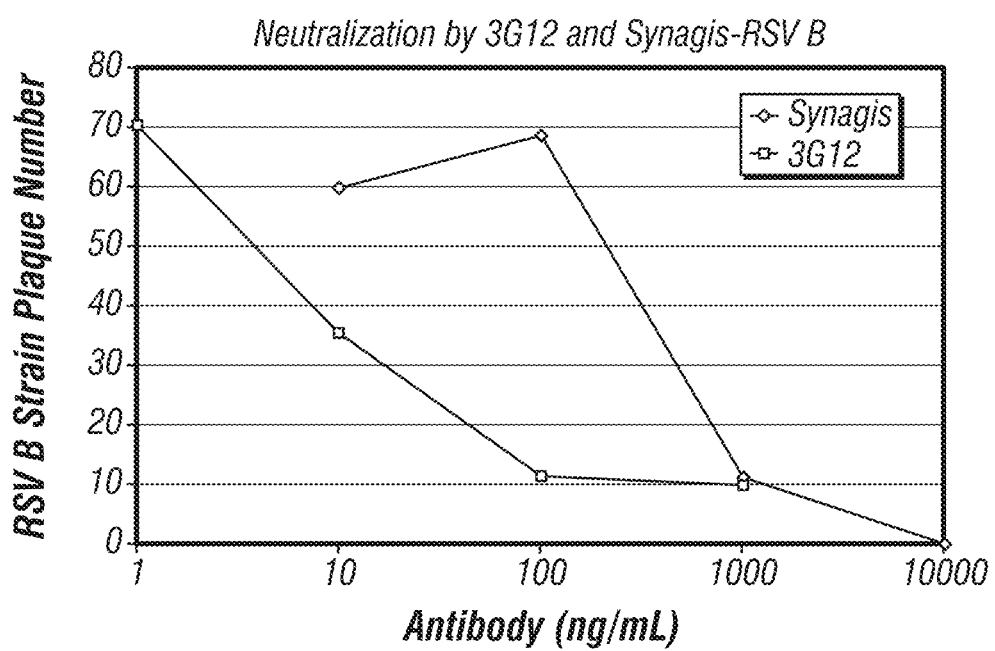
FIG. 11 shows a comparison of antibody 3G12 of the invention with Synagis® in neutralizing RSV strain B.

FIG. 11 shows neutralization of 3G12 antibody with respect to strain B, in comparison with Synagis®. The normalized data (% of control) are based on an absolute plaque number of 160-180 per experiment. The antibodies of the invention, with in vitro affinities from 1 pM up to 5 nM (Table 1), have EC$_{50}$ values between 10-100 ng/ml.

EXAMPLE 7

Anti-G Prophylaxis in Mice

The invention antibodies, Synagis®, and human IgG1 were tested for their ability to prevent RSV infection in mice. On day −1, prior to infection, mice in the control group were injected i.p. with medium and PBS. In test groups, injection was of 0.15, 1.5 and 15 mg/kg of antibodies hIgG1 (non-immune, isotype control), or 3G12 or 3D3 or Synagis®. This amounts to approximately 3 µg, 30 µg and 300 µg per mouse.

On day 0, the mice were inoculated with 1×10$^6$pfu RSV long-strain by intranasal administration. On days 0 and 5, the lungs, bronchial alveolar lavage (BAL) and serum were collected and body weight, lung weight, pfu in the lung lobe section, viral load (by qPCR), lung histology, total leukocytes, FACS, and IFN$^G$ in BAL were all measured.

Figure 12:
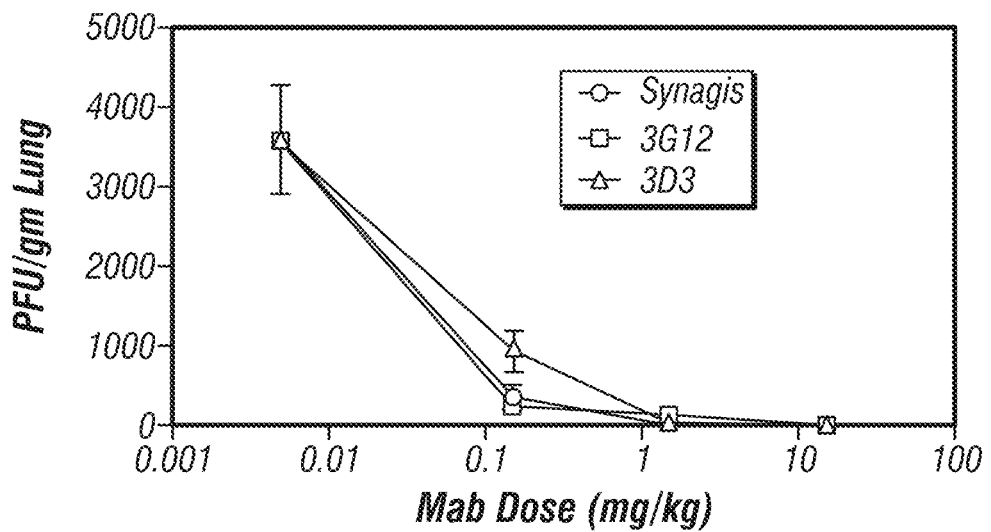
FIG. 12 shows a comparison of the prophylactic activity of two invention antibodies with Synagis® commercial antibody.

FIG. 12 shows the results based on viral lung load using the plaque assay from the foregoing list. The data in FIG. 12 show that 3G12 and 3D3 are equally effective as Synagis® in this assay. (A typical human dose for Synagis® is 15 mg/kg in humans.)

EXAMPLE 8

Therapeutic Efficacy of Antibodies to RSV-Ga/Gb

Figure 13A:
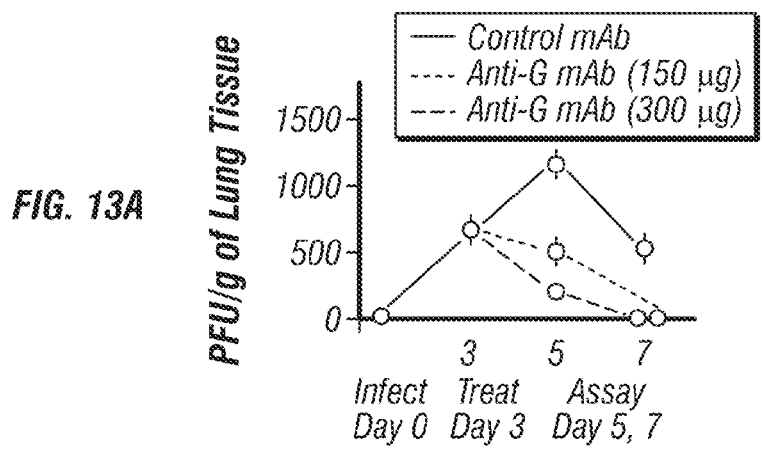
FIGS. 13A-13C show therapeutic efficacy of mAb 131-2G in a post-infection murine model of RSV (treatment at day +3 post-infection), including dose dependent reduction in viral load (panel A) along with other measures of reduced lung inflammation: NK cells and PMN cells (panel B) and interferon-gamma (IFN$^G$) (panel C).

Antibodies to the conserved motif on RSV-G are shown to have therapeutic efficacy. Mice were infected intra-nasally at day 0 with 10$^6$ pfu of RSV, then treated at day 3 with 3 mg/kg of antibody injected i.p. and assayed at days 5 and 7 for viral load in bronchial alveolar lavage. In this model, the infection is more readily cleared naturally than in humans. Nonetheless, the antibody treatment causes acceleration in viral clearance in a dose dependent fashion as compared to a control antibody that does not bind RSV (FIG. 13A). Each treatment group had 5 animals, and the results are statistically significant.

Figure 13B:
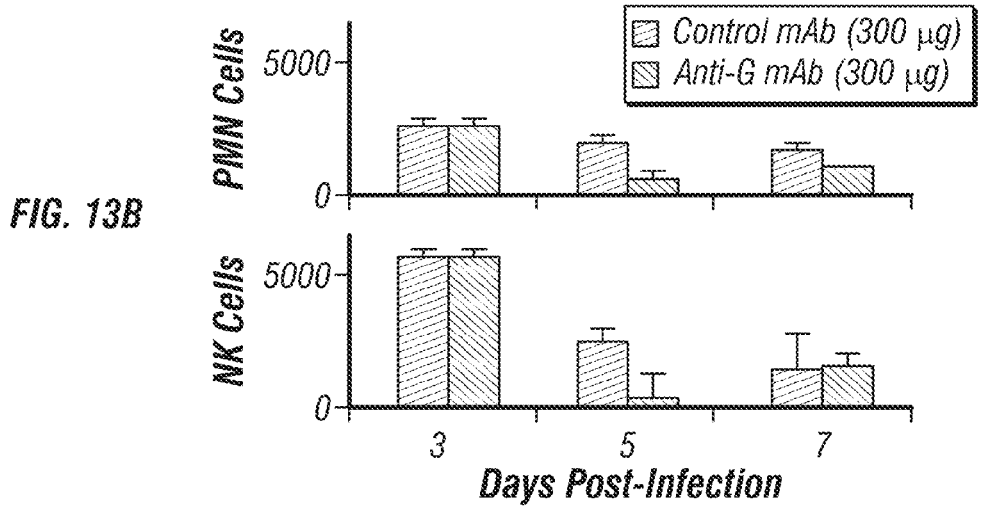
Figure 13C:
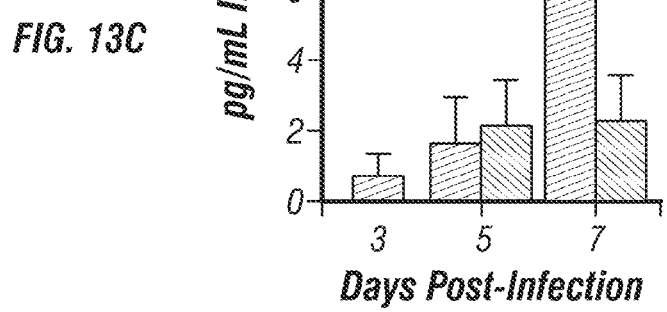

As described in WO 00/43040, antibodies to Substance P are beneficial in alleviating the lung inflammation caused by RSV, an animal model for the prolonged morbidity that is the clinically important feature of RSV infection. Up regulation of Substance P is dependent on active G protein (Haynes, L. M., et al., *J. Virol.* (2003) 77:9831-9844). Reduction in measures of lung inflammation following treatment with an antibody of the invention have also been observed, including reduction in inflammatory NK and total PMN cells (FIG. 13B), as well as reduction in cytokines, e.g., IFN$^G$ (FIG. 13C).

In an additional test, on day 0, mice were inoculated with 10$^6$ pfu of RSV A-type long strain by intranasal administration.

On day 3, various groups of 4-5 mice were treated as follows:

Group 1: control group which did not receive infection on day 0 and was treated with PBS.

Group 2: negative control which received RSV inoculation on day 0 and PBS treatment on day 3.

Group 3: RSV inoculation on day 0 and Synagis® antibody i.p. in saline at 1, 10, or 100 µg per mouse or 0.05, 0.5 or 5 mg/kg.

Group 4: RSV inoculated on day 0 and administered mAb 3D3 in the same protocol as Group 3.

Group 5: received RSV inoculation on day 0 and administered 3G12 in the same amounts as Groups 3 and 4.

Figure 14:
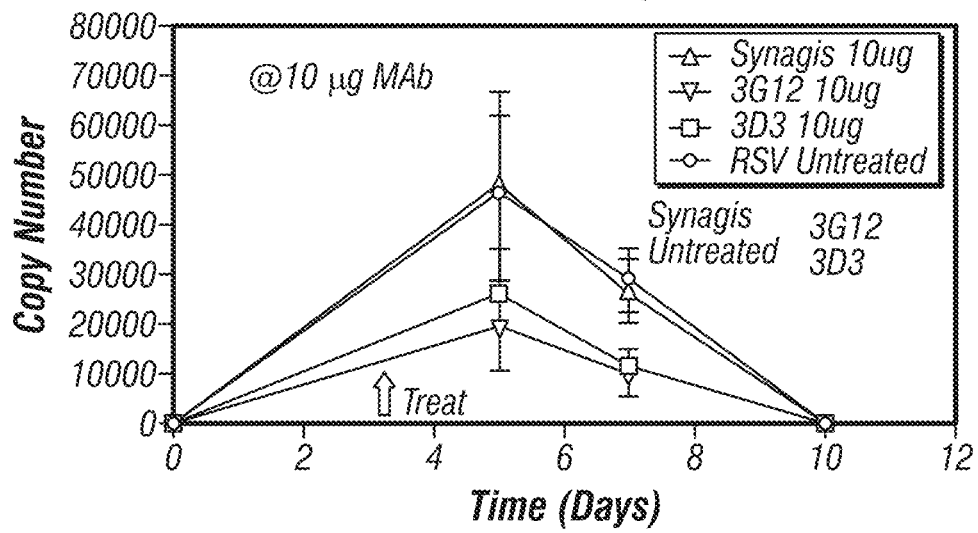
FIG. 14 shows the time course of viral titer in a mouse model treated with 3G12, 3D3 or Synagis® antibodies at a low dose that highlights the potency advantage of the high affinity antibodies of the invention.

Lungs and BAL fluid were collected on days 0, 3, 5, 7 and 10. In addition, body weight, lung weight, pfu in lung lobes, viral load by qPCR, lung histology, total leukocytes, FACS were measured as well as IFN$^G$ in BAL. The results for qPCR in the groups administered 10 µg of mAb are shown in FIG. 14.

As shown, the viral titer in Synagis®-treated and untreated mice behaves similarly at this relatively low dose of antibody, whereas both 3D3 treated and 3G12 treated mice had greatly lower titers at the peak of infection on day 5. This experiment verifies that higher affinity in vitro correlates with higher potency in vivo.

Figure 15:
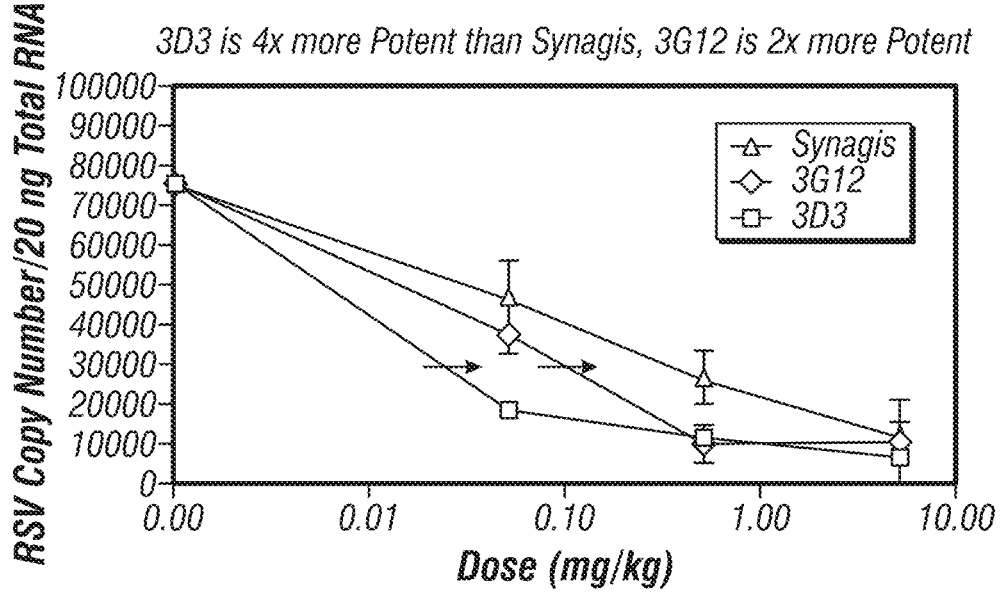
FIG. 15 is a dose/response curve measuring the effect of antibodies on RSV copy number in the lungs of RSV-infected mice when treated at day +3 after infection.

FIG. 15 shows the dose response curve demonstrating that 3G12 and 3D3 were able to lower the RSV copy number as measured by qPCR on day 7 at lower concentrations than Synagis®. 3D3 was particularly potent, again consistent with having higher affinity in vitro.

Figure 16:
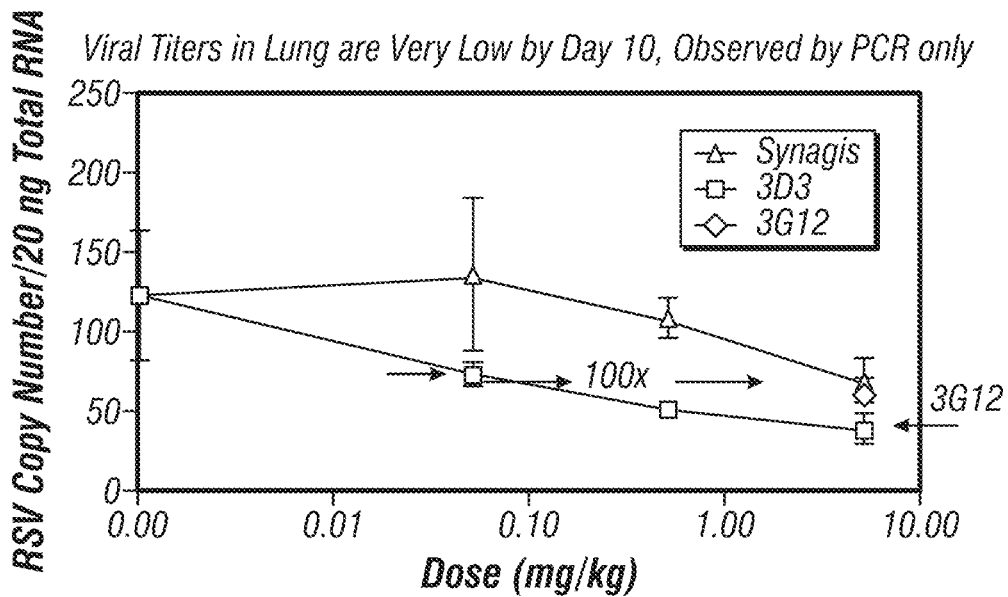
FIG. 16 shows comparative ability of Synagis®, 3D3 and 3G12 to reduce viral load at the end stages of infection, after treatment at day +3 after infection.

Similarly, when qPCR viral counts are measured on day 10, although viral titers are naturally very low at this point due to natural clearance by the mouse immune system, 3D3 is approximately 100 times more potent than Synagis® at the various dose concentrations as shown in FIG. 16. This experiment highlights the utility of high affinity antibodies, which continue to be effective even when the antigen concentration drops. The human disease course is considerably more prolonged than in the mouse, providing a clear motivation for use of an antibody that continues to neutralize virus for an extended time period.

In still further experiments, mice were treated with murine anti-G mAb or murine anti-F mAb in groups of four, each experiment repeated three times. The mice were immunized on day 0 and treated with the antibodies on day 3, and various indications of efficacy were measured at days 3, 5 and 7.

Figure 17:
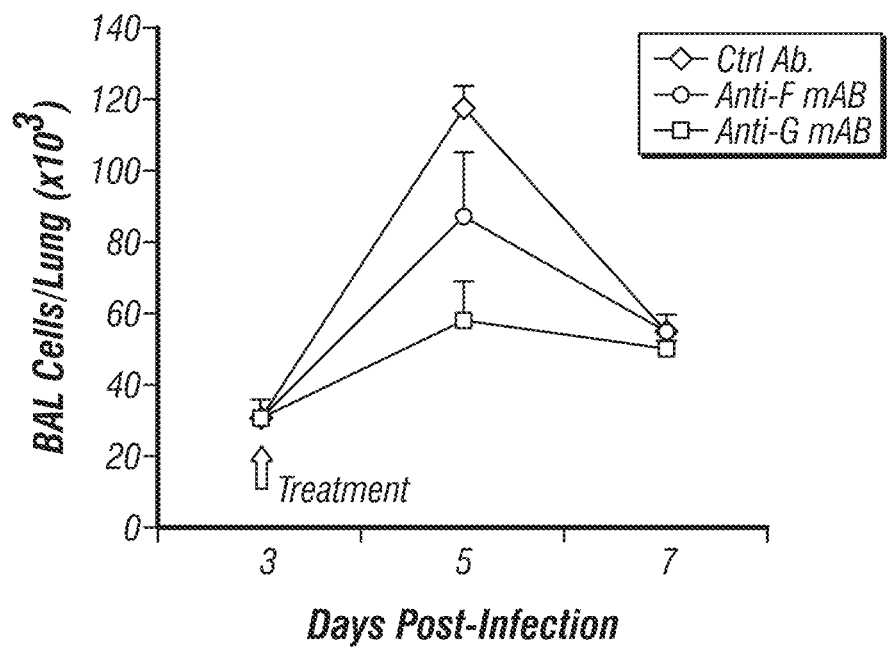
FIG. 17 shows the effect of control antibody, anti-F antibody and anti-G antibody on BAL cells in the lungs of RSV-infected mice. Treatment was at day +3 post-infection.

As one index of effectiveness, inflammatory cells in the bronchial alveolar lavage (BAL) were measured in the three groups with the results shown in FIG. 17. BAL cells per lung are plotted on the Y-axis from 0 to $140\times10^3$. The results show anti-F mAb lowered the BAL cells per lung at day 5 as compared to isotype control non-immune antibody, whereas anti-G mAb lowered the BAL cell count substantially more. By day 7, the infection had run its course.

Figure 18:
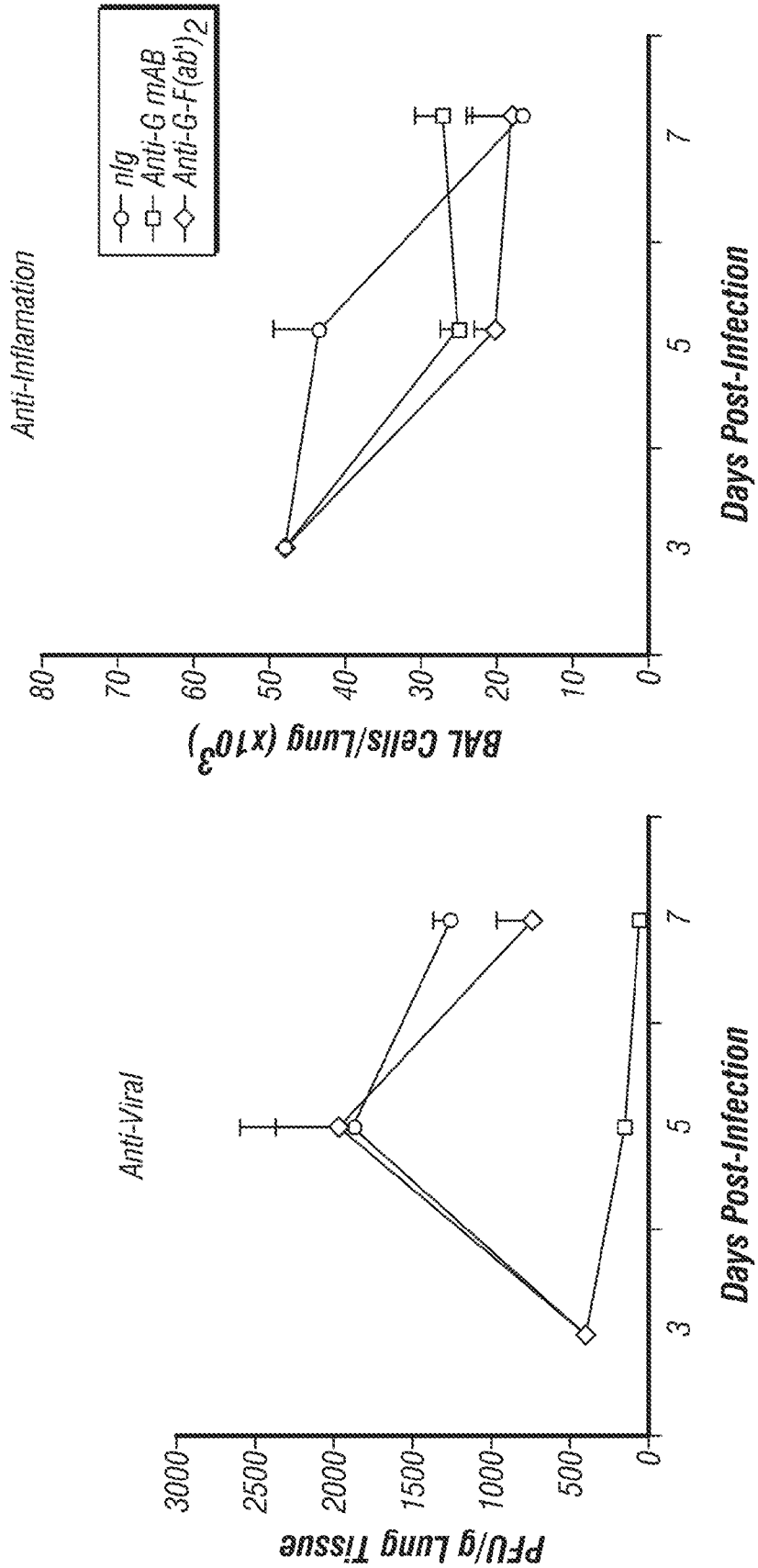
FIGS. 18A and 18B show that F(ab')$_2$ immunospecific fragments of anti-G mAb are as effective as the intact mAbs in reducing inflammation in RSV-infected mice when given at day +3 post-infection, but are not effective in reducing viral load.

FIGS. 18A and 18B show a comparison of effectiveness of anti-G mAb (murine 131-2G) compared with anti-G F(ab')$_2$ obtained from this antibody by cleavage with pepsin and removal of the Fc fragments using immobilized Protein A. It has been shown that complement is important for the anti-viral effect of anti-G antibodies in vitro. This is confirmed in FIG. 18A where the anti-viral effect is measured as pfu/g lung tissue. Assays were conducted as in Example 6. The F(ab')$_2$ fragment of an anti-G antibody, which lacks the Fc portion of IgG that is needed for complement mediated activity, is little better than control in lowering viral load, while anti-G mAb is very effective. However, when inflammation is used as a measure of results, as shown in FIG. 18B, the F(ab')$_2$ fragment of anti-G mAb is fully as effective as the complete antibody. This experiment establishes that neutralization of the G protein is critical to reducing airway inflammation.

Since the virus actively secretes a soluble form of the G protein, and high affinity binding is important for neutralization of soluble factors, the high affinity antibodies of the invention are expected to have particular utility for the anti-inflammatory effect.

Figure 19:
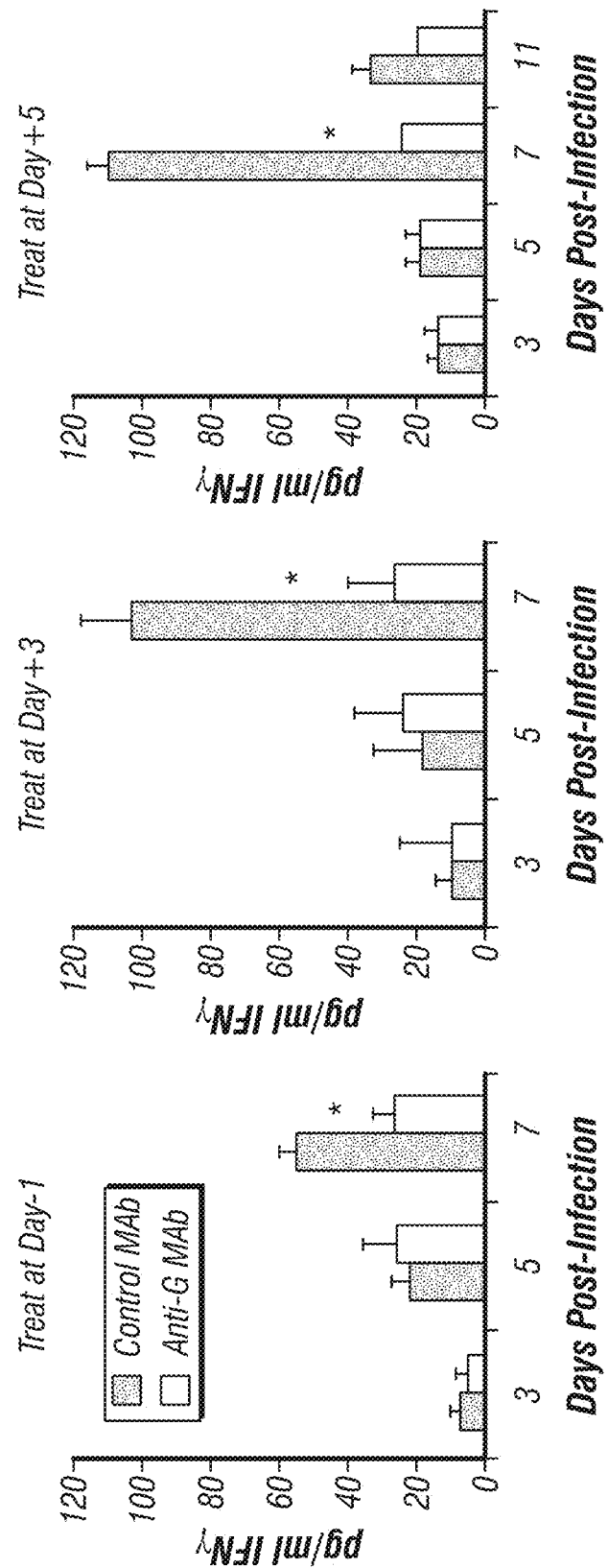
FIGS. 19A-19C show the effect of anti-G mAbs on the production of IFN$^G$ in BAL at various times of administration of the antibody, ranging from prophylactic (day −1) to day +3 and day +5 post-infection.

FIGS. 19A, B and C show the effect of anti-G mAb on the production of IFN$\gamma$ in BAL as a function of time of administration, with the cytokine serving as a marker for airway inflammation. Control non-immune antibody in all cases fails to reduce the increase in IFN$\gamma$ production that accompanies airway inflammation. However, whether anti-G mAb is administered at day −1 (panel A), at day +3 (panel B) or even at day +5 (panel C), a dramatic decrease in the level of IFN$\gamma$ at day 7 results. This experiment establishes utility of antibodies to the central conserved motif of the RSV G protein for treating inflammation well past the peak of viral load.

EXAMPLE 9

Specificity of Endogenous Antibodies in Infected Subjects

Serum samples from four elderly adults with severe RSV disease and with six elderly adults with mild RSV disease were tested for immunoreactivity with the synthetic peptide (SEQ ID NO:16):

```
Ac-Lys-Pro-Asn-Asn-Asp-Phe-His-Phe-Glu-Val-Phe-Asn-Phe-Val-Pro-Cys-Ser-
                                                                      |
                                                    |
     Ile-Cys-Ser-Asn-Asn-Pro-Thr-Cys-Trp-Ala-Ile-Cys-Lys-Arg-Ile-NH2
     |_____|
```

Figure 20:
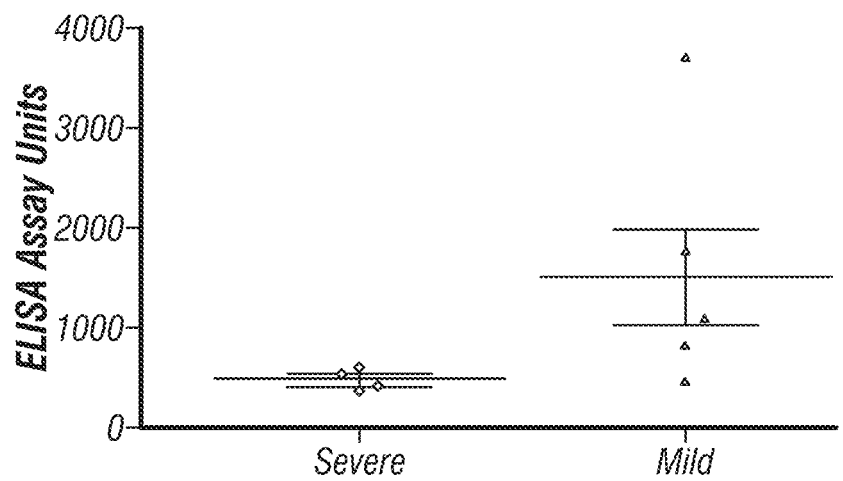
FIG. 20 shows antibody titer to the central conserved region of RSV G protein from elderly patients infected with RSV. The patients were selected according to severity of clinical signs and symptoms, severe or mild. The absence of appreciable titer to the central conserved region is correlated with severe disease.

(disulfide bridges as shown)

which represents the conserved region of RSV G protein from strain A2. The assay was performed using the ELISA protocol described in Example 5. The levels of antibodies immunoreactive with this peptide correlate with the severity of the disease wherein subjects with mild forms of the disease exhibited much higher titers than subjects with more severe manifestations of the infection (see FIG. 20). These results indicate that antibodies immunoreactive with this portion of the G protein are effective in ameliorating infection.

The invention claimed is:

1. An isolated monoclonal antibody (mAb) which is 3D3 or 2B11 wherein the light chain variable region (VL) has the amino acid sequence SEQ ID NO:45 and the heavy chain variable region (VH) has the amino acid sequence SEQ ID NO:31 (3D3) or the VL has the amino acid sequence SEQ ID NO:47, and the VH has the amino acid sequence SEQ ID NO:33 (2B11) each VL coupled to human kappa or lambda constant region and each VH coupled to human IgG1 constant region, or an immunoreactive fragment thereof which is a single chain form.

2. The mAb of claim 1 which is a complete antibody which is recombinantly produced by a process which comprises fusing a nucleotide sequence encoding the variable regions of 3D3 or 2B11 to said human constant regions.

3. One or more nucleic acid molecules that comprise (an) expression system(s) which comprise(s) first nucleotide sequence(s) that encode(s) an mAb wherein the light chain variable region (VL) has the amino acid sequence SEQ ID NO:45 and the heavy chain variable region (VH) has the amino acid sequence SEQ ID NO:31 (3D3) or the VL has the amino acid sequence SEQ ID NO:47, and the VH has the amino acid sequence SEQ ID NO:33 (2B11) or fragment thereof or one or more nucleic acid molecule(s) that comprise(s) second nucleotide sequence(s) complementary to said first nucleotide sequence(s) over its(their) entire length; said encoding nucleotide sequence(s) or complement(s) operably linked to heterologous control sequences for expression.

4. Recombinant host cells that contain the expression system of claim 3.

5. A method to produce mAb 3D3 or 2B11 or immunoreactive fragment thereof, which method comprises culturing the cells of claim 4 and recovering said mAb or fragment.

6. A transgenic non-human animal or transgenic plant that produces an mAb wherein the light chain variable region (VL) has the amino acid sequence SEQ ID NO:45 and the heavy chain variable region (VH) has the amino acid sequence SEQ ID NO:31 (3D3) or the VL has the amino acid sequence SEQ ID NO:47, and the VH has the amino acid sequence SEQ ID NO:33 (2B11) or fragment thereof.

7. A pharmaceutical composition that contains a therapeutically or prophylactically effective amount of an isolated monoclonal antibody wherein the light chain variable region (VL) has the amino acid sequence SEQ ID NO:45 and the heavy chain variable region (VH) has the amino acid sequence SEQ ID NO:31 (3D3) or the VL has the amino acid sequence SEQ ID NO:47, and the VH has the amino acid sequence SEQ ID NO:33 (2B11) or fragment thereof, along with a pharmaceutically acceptable excipient, wherein said effective amount is sufficient to provide a dosage of 0.1-50 mg/kg.

8. The pharmaceutical composition of claim 7 that further contains an additional pharmaceutical agent other than an antibody immunoreactive with RSV, along with a pharmaceutically acceptable excipient.

9. The composition of claim 8 wherein said additional agent is an anti-RSV drug.

10. The pharmaceutical composition of claim 7 which further contains one or more monoclonal antibodies or fragments thereof immunoreactive with the F protein of RSV.

11. A method to treat RSV in a subject infected with RSV, which method comprises administering to a subject in need of such treatment and who is infected with RSV a pharmaceutical composition which comprises an effective amount of an mAb wherein the light chain variable region (VL) has the amino acid sequence SEQ ID NO:45 and the heavy chain variable region (VH) has the amino acid sequence SEQ ID NO:31 (3D3) or the VL has the amino acid sequence SEQ ID NO:47, and the VH has the amino acid sequence SEQ ID NO:33 (2B11).

12. The method of claim 11 wherein the subject is human.

13. The method of claim 12 which further includes administering an additional pharmaceutical agent other than an antibody immunoreactive with RSV, along with a pharmaceutically acceptable excipient.

14. The method of claim 12 which further includes administering one or more monoclonal antibodies or fragments thereof immunoreactive with the F protein of RSV.

15. A method to reduce airway inflammation in a human subject infected with RSV, which comprises administering to a subject in need of such reduction a pharmaceutical composition which comprises an effective amount of an mAb wherein the light chain variable region (VL) has the amino acid sequence SEQ ID NO:45 and the heavy chain variable region (VH) has the amino acid sequence SEQ ID NO:31 (3D3) or the VL has the amino acid sequence SEQ ID NO:47, and the VH has the amino acid sequence SEQ ID NO:33 (2B11).

16. A method to enhance resistance to infection by RSV in a human subject, which comprises administering to a subject in need of such enhancement a pharmaceutical composition which comprises an effective amount of an mAb wherein the light chain variable region (VL) has the amino acid sequence SEQ ID NO:45 and the heavy chain variable region (VH) has the amino acid sequence SEQ ID NO:31 (3D3) or the VL has the amino acid sequence SEQ ID NO:47, and the VH has the amino acid sequence SEQ ID NO:33 (2B11).

* * * * *